United States Patent
Wolpo

(10) Patent No.: US 9,907,633 B2
(45) Date of Patent: Mar. 6, 2018

(54) ORAL CARE SYSTEM WITH MOUTHPIECE

(71) Applicant: Stephen H. Wolpo, Stamford, CT (US)

(72) Inventor: Stephen H. Wolpo, Stamford, CT (US)

( * ) Notice: Subject to any disclaimer, the term of this patent is extended or adjusted under 35 U.S.C. 154(b) by 466 days.

(21) Appl. No.: 14/540,797

(22) Filed: Nov. 13, 2014

(65) Prior Publication Data
US 2015/0072300 A1 Mar. 12, 2015

Related U.S. Application Data

(63) Continuation-in-part of application No. 14/038,186, filed on Sep. 26, 2013.
(Continued)

(51) Int. Cl.
*A61C 3/00* (2006.01)
*A61C 17/22* (2006.01)
(Continued)

(52) U.S. Cl.
CPC ........ *A61C 17/228* (2013.01); *A46B 15/0008* (2013.01); *A46B 15/0012* (2013.01);
(Continued)

(58) Field of Classification Search
CPC ......... A61C 17/20; A61C 17/22; A61C 17/28; A61C 17/30; A61C 17/221; A61C 17/222; A61C 17/227
(Continued)

(56) References Cited

U.S. PATENT DOCUMENTS 3,215,139 A 11/1965 Dietz
3,401,690 A * 9/1968 Martin ................ A61C 17/20
433/119

(Continued)

FOREIGN PATENT DOCUMENTS

WO 2004108008 A1 12/2004
WO 2012088193 A2 6/2012

OTHER PUBLICATIONS

International Search Report and Written Opinion of the International Searching Authority Application No. PCT/US2013/062219 Completed: Feb. 10, 2014; dated Feb. 24, 2014 10 pages.

*Primary Examiner* — Cris L Rodriguez
*Assistant Examiner* — Matthew Saunders
(74) *Attorney, Agent, or Firm* — St. Onge Steward Johnston & Reens, LLC

(57) ABSTRACT

An oral care system for cleaning teeth and gums includes a housing, an oral hygiene unit, and a gooseneck arm attached to the housing and releasably coupling the oral hygiene unit to the housing, the gooseneck arm being adjustable to hold the oral hygiene unit at a defined position and orientation relative to the housing. The oral hygiene unit has a mouthpiece having at least one arcuate channel adapted to receive and surround the teeth. The mouthpiece includes at least two modalities chosen from a group consisting of a mechanical modality, an iontophoretic modality, and a disinfection modality, wherein the mechanical modality brushes the teeth and gums and dislodges food debris, the iontophoretic modality breaks up plaque buildup, and the disinfection modality removes the food debris and plaque. The oral care system includes a control unit which controls transmission of the modalities and tracks utilization of the system.

23 Claims, 12 Drawing Sheets

Related U.S. Application Data

(60) Provisional application No. 61/707,550, filed on Sep. 28, 2012.

(51) Int. Cl.

| | | |
|---|---|---|
| *A61C 17/02* | (2006.01) | |
| *A61C 17/34* | (2006.01) | |
| *A61N 1/05* | (2006.01) | |
| *A61N 1/32* | (2006.01) | |
| *A46B 15/00* | (2006.01) | |
| *A61N 1/04* | (2006.01) | |
| *A61C 17/20* | (2006.01) | |

(52) U.S. Cl.
CPC ...... *A61C 17/0211* (2013.01); *A61C 17/0217* (2013.01); *A61C 17/221* (2013.01); *A61C 17/3481* (2013.01); *A61N 1/0428* (2013.01); *A61N 1/0548* (2013.01); *A61N 1/325* (2013.01); *A61C 17/20* (2013.01)

(58) Field of Classification Search
USPC .......................................... 433/32, 80, 216
See application file for complete search history.

(56) References Cited

U.S. PATENT DOCUMENTS

| | | | |
|---|---|---|---|
| 3,440,680 A * | 4/1969 | Werding | A46B 9/045 15/24 |
| 3,489,141 A | 1/1970 | Warren, Jr. | |
| 3,520,297 A | 7/1970 | Bechtold | |
| 3,566,869 A | 3/1971 | Crowson | |
| 3,731,675 A * | 5/1973 | Kelly | A61C 17/0211 601/164 |
| 4,011,616 A * | 3/1977 | Kennedy | A46B 9/045 15/21.1 |
| 4,224,710 A | 9/1980 | Solow | |
| 4,237,574 A | 12/1980 | Kelly et al. | |
| 4,244,373 A | 1/1981 | Nachman | |
| 5,337,435 A | 8/1994 | Krasner et al. | |
| 5,365,624 A | 11/1994 | Berns | |
| 5,443,386 A | 8/1995 | Viskup | |
| 6,152,733 A | 11/2000 | Hegemann et al. | |
| 6,416,166 B1 * | 7/2002 | Robinson | B41J 2/1752 347/19 |
| 6,505,926 B1 * | 1/2003 | Trafton | B41J 2/17513 347/86 |
| 6,616,447 B1 * | 9/2003 | Rizoiu | A61C 19/063 433/216 |
| 6,893,259 B1 * | 5/2005 | Reizenson | A61C 17/0211 433/29 |
| 7,044,737 B2 | 5/2006 | Fu | |
| 7,118,377 B2 | 10/2006 | Inoue etal. | |
| 7,499,760 B2 * | 3/2009 | Rose | A61O 5/00 433/215 |
| 7,537,451 B1 | 5/2009 | Ramnarine | |
| 8,241,035 B2 | 8/2012 | Jones et al. | |
| 9,168,370 B2 * | 10/2015 | Nemeh | A61C 19/063 |
| 2003/0203336 A1 * | 10/2003 | Somodi | A61C 17/043 433/91 |
| 2005/0151810 A1 * | 7/2005 | Graham | B41J 2/17523 347/86 |
| 2007/0009856 A1 * | 1/2007 | Jones | A61C 17/20 433/215 |
| 2007/0184404 A1 | 8/2007 | Johnki | |
| 2008/0003540 A1 * | 1/2008 | Khawaled | A61C 19/066 433/215 |
| 2008/0032252 A1 * | 2/2008 | Hayman | A61B 5/0088 433/29 |
| 2008/0199830 A1 * | 8/2008 | Fontenot | A46B 5/0012 433/215 |
| 2008/0227046 A1 * | 9/2008 | Lowe | A61C 7/00 433/2 |
| 2009/0117513 A1 * | 5/2009 | Nemeh | A61C 19/063 433/32 |
| 2009/0142724 A1 * | 6/2009 | Rosenblood | A61B 1/24 433/29 |
| 2009/0208898 A1 | 8/2009 | Kaplan | |
| 2009/0276972 A1 | 11/2009 | Dugan | |
| 2010/0324460 A1 | 12/2010 | Van Der Rijt et al. | |
| 2011/0072605 A1 | 3/2011 | Steur | |
| 2011/0154595 A1 | 6/2011 | Hill | |
| 2011/0247159 A1 | 10/2011 | Steur et al. | |
| 2011/0258792 A1 | 10/2011 | Steur et al. | |
| 2011/0318705 A1 | 12/2011 | Sullivan et al. | |
| 2012/0077144 A1 | 3/2012 | Fougere et al. | |
| 2012/0141954 A1 | 6/2012 | Headstrom et al. | |
| 2012/0189976 A1 | 7/2012 | McDonough et al. | |
| 2013/0236851 A1 * | 9/2013 | McDonough | A61C 17/0208 433/89 |
| 2013/0260332 A1 | 10/2013 | Shapiro | |
| 2013/0323669 A1 * | 12/2013 | Lowe | A61C 7/00 433/24 |
| 2014/0093832 A1 * | 4/2014 | Nemeh | A61C 19/063 433/1 |
| 2015/0024340 A1 | 1/2015 | De Gentile | |

\* cited by examiner

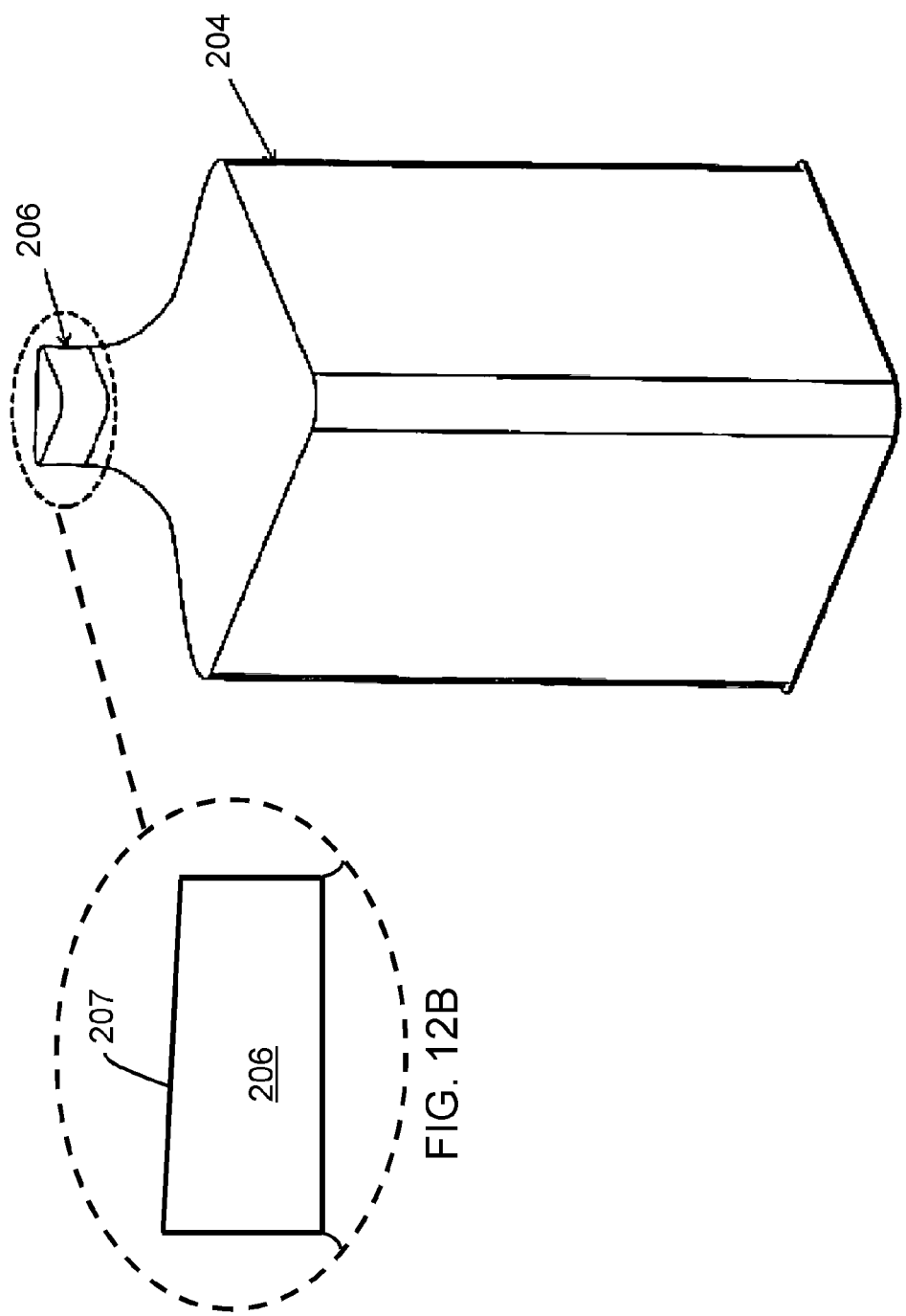

ORAL CARE SYSTEM WITH MOUTHPIECE

FIELD OF THE INVENTION

This invention relates to a dental hygiene system and more specifically to a hands-free oral hygiene system that maintains or improves a user's oral health by breaking down and removing plaque from the teeth and gums, brushing the teeth and gums, and irrigating the teeth and gums with disinfecting fluid.

BACKGROUND OF THE INVENTION

It is well known that an effective method of maintaining oral hygiene is cleaning the teeth and gingival regions on a daily basis. The conventional method of cleaning teeth involves flossing the teeth as well as brushing the teeth and gums with dentifrice (e.g., toothpaste, tooth powder) using a toothbrush. In addition to brushing the teeth, the conventional method may include the step of rinsing the teeth and gums with antiseptic fluid or mouthwash to kill bacterial plaque which can cause white-spot lesions, dental caries (e.g., tooth decay and cavities), and gingivitis. However, the conventional method of oral care requires a significant number of steps involving coordinated movement of the hands and mouth. For example, a person must stand in front of a mirror, tear a piece of floss, insert the floss between the teeth gently sliding the floss up and down, curve the floss around the base of each tooth, making sure the floss goes beneath the gumline, thereafter grip a tooth brush, apply toothpaste to the bristles of the toothbrush, properly orient the toothbrush so that the bristles contact the surfaces of the teeth (e.g., buccal, labial, lingual, occlusal) as well as the gum line, perform a repetitive brushing motion for at least two minutes, and then expel toothpaste suds. Further, the person must measure an amount of mouthwash, pour it into the mouth, gargle for a period of time, and thereafter expel the spent mouthwash.

Because the conventional form of oral care involves laborious steps and requires substantial dexterity in maneuvering a cleaning device (e.g., toothbrush), people suffering from physical and/or mental disabilities fail to properly clean their teeth. In some situations, seniors and handicapped people, such as amputees, people suffering impairments or paralysis in the arms and/or hands, and people suffering from developmental disabilities (e.g., autism, cerebral palsy, Down syndrome) are unable to perform the conventional oral care method because they either have limited dexterous abilities in their hands/arms or lack the mental capacity to perform the steps involved therein. Consequently, another person (e.g., caregiver, healthcare professional) must brush and floss the teeth of the senior or handicapped person. With regard to amputees having prosthetic hands and/or hooks, these artificial limbs are unable to firmly grip small or thin items, like a toothbrush. Controlling a toothbrush with artificial limbs has proven to be difficult, especially since the toothbrush often slips out of the prosthesis. In short, there lacks effective oral care for people who lack dexterous abilities.

In order to promote improved oral care, dental devices have been developed which simplify the steps needed to properly clean teeth. For example, U.S. Pat. No. 4,237,574 to Kelly et al. discloses a mouthpiece with a plurality of brush heads disposed along an inner channel and ultrasonic means for vibrating the brush heads. Kelly further discloses a different mouthpiece, wherein, instead of using brush heads, a fluid medium is supplied to and discharged from the mouth piece, wherein the fluid medium is used to transmit ultrasonic energy to the teeth. These two devices, however, fail to clean between the teeth, where buildup of plaque and food debris is common. The bristles on the brush heads do not extend and reach between the teeth. Further, the mere use of a fluid medium to clean the teeth is not as effective as scrubbing them with brush heads. In other words, the energy transmitted by the fluid to the teeth during rinsing is not sufficient alone to break up plaque deposits on the teeth. Moreover, the two devices still require a person to use his/her hands to hold and insert the mouthpiece into a mouth prior to cleaning and remove the mouthpiece after cleaning.

U.S. Pat. No. 7,118,377 to Inoue et al. and U.S. Pat. No. 6,893,259 to Reizenson and U.S. Patent Application No. 2011/0318705 to Sullivan et al. each describe a dental system adapted to clean a person's teeth and gingival regions using a disinfection modality. Each system comprises a mouthpiece, a supply tube connecting the mouthpiece to a supply unit, a drain tube connecting the mouthpiece to a drain unit, and a pump unit for introducing a cleaning solution into the mouthpiece through the supply tube and removing spent solution through the drain tube. However, the systems disclosed in these references fail to provide adequate means for removing plaque on the surfaces of teeth, in the gingival crevices between the teeth and gums, and in the teeth crevices. It is generally agreed upon that the mere use of a cleaning solution, such as mouthwash, does not provide an effective means of cleaning teeth and does not eliminate the need for brushing and flossing. Moreover, these systems cannot be easily used by people who have limited dexterity. Each system still requires that a person (either a caregiver or the person with limited dexterous abilities) hold and insert the mouthpiece into the mouth before starting a cleaning session and remove the mouthpiece from the mouth after the cleaning session has ended. In addition, because of the weight of components that are attached to the mouthpiece, it is sometimes necessary for one to hold the mouthpiece constantly during a cleaning session in order to reduce any undue force, pressure, and/or stress exerted on the mouth.

While the prior art dental systems provide some benefits in oral maintenance, they still suffer from several disadvantages. One major disadvantage is that these dental systems are not designed for people who lack dexterity, including handicapped people, amputees, people suffering impairments or paralysis in the arms and/or hands, and people suffering from developmental disabilities. Prior art dental systems are not hands-free and still require a person to hold and insert the dental device into the mouth and hold the device stable within the mouth during a cleaning session. With respect to conventional toothbrushes, a person must also manually brush the teeth. Another disadvantage is that the prior art dental systems fail to effectively clean the crevices between teeth where plaque and food debris commonly accumulate. Further, the prior art dental systems do not provide a comprehensive, synergistic treatment of the teeth and gums, which includes plaque-removing, cleaning, disinfecting, and preventative modalities.

SUMMARY OF THE INVENTION

Accordingly, it is an object of the present invention to provide a hands-free oral hygiene system which is adapted to clean teeth and promote oral care for people with physical and mental disabilities, including people who are handicapped or lack dexterity in performing tasks with their arms and hands.

It is an object of the present invention to provide a hands-free oral hygiene system which cleans teeth without requiring a person to constantly hold a cleaning device within a mouth using a hand during a cleaning session.

It is another object of the present invention to provide a hands-free oral hygiene system which does not require a person to hold and insert a cleaning device into the mouth of another person, such as one who lacks dexterous abilities.

It is another object of the present invention to provide an oral hygiene system which cleans the surfaces of teeth (e.g., buccal, labial, lingual, occlusal), the gingival crevices, and the crevices between teeth.

It is a further object of the present invention to provide an oral hygiene system which removes plaque and food debris from the teeth as well as cleans, disinfects and applies protective elements to the teeth. It is also an object of the present invention to perform the above tasks in a coordinated manner—for example, simultaneously—in order to achieve a synergistic effect.

It is yet another object of the present invention to provide an oral hygiene system which removes plaque and food debris from the teeth as well as cleans, disinfects and applies protective elements to a plurality of teeth and more specifically to an entire row of teeth (i.e., maxillary/upper teeth, mandibular/lower teeth).

It is another objective of the present invention to provide an oral hygiene system which can monitor and track utilization and treatment sessions as well as track and collect patient care information.

These and other objectives are achieved by providing a hands-free oral hygiene system for cleaning teeth and gums, wherein the system includes a mouthpiece which has at least one arcuate channel adapted to receive and surround the teeth and which transmits at least two modalities chosen from a group consisting of a mechanical modality, an iontophoretic modality, and a disinfection modality. The mechanical modality brushes the teeth and gums and dislodges food debris. The iontophoretic modality breaks up plaque and food debris that has built up on the surfaces of the teeth, in the gingival crevices between the teeth and gum line, and in the crevices between adjacent teeth. The disinfection modality irrigates the teeth and gums in order to remove any food debris and plaque buildup. In addition, the disinfection modality is adapted to kill bacteria present on the teeth and gums and apply a protective layer on the teeth to prevent tooth decay and/or gingivitis.

Noted herein, the terms "transmit" and "transmission" are used interchangeably with the words "provide" and "provision" and thus signify the provision of a modality.

Other objectives of the invention are achieved by providing an oral hygiene system for maintaining oral care of teeth and gums, wherein the system includes a mouthpiece for receiving and surrounding the teeth and gums, the mouthpiece being adapted to include and transmit in a coordinated sequence at least two modalities chosen from a group consisting of a mechanical modality, an iontophoretic modality, and a disinfection modality. The transmission or provision of the at least two modalities provides a comprehensive, synergistic oral care treatment, thereby maintaining or improving the health of the teeth and gums. In some embodiments, the at least two modalities are transmitted simultaneously. In other embodiments, the coordinated sequence is defined by a sequential transmission of the at least two modalities by the mouthpiece.

The coordinated sequence may be defined by the length of time in which any one of the at least two modalities is used to treat the teeth and gums. In a preferred embodiment, the overall oral treatment provided by the oral hygiene system lasts for at least two minutes. However, in some embodiments, the time with which the oral hygiene system cleans the teeth and gums may be less than two minutes. The oral hygiene system is able to sufficiently clean the teeth and gums in less than two minutes due to the synergistic effect of transmitting the at least two modalities.

Additional objectives of the invention are achieved by providing an oral hygiene system having a mouthpiece with at least one arcuate channel for receiving and surrounding the teeth and gums and at least one structural rim, wherein the structural rim is adapted to make sealing contact with the gums. The at least one arcuate channel and the at least one structural rim, subsequently, form a sealed enclosure or chamber around the teeth. The sealed enclosure is adapted to direct and focus the transmission of at least two modalities chosen from the group consisting of a mechanical modality, an iontophoretic modality, and a disinfection modality. The beneficial effects provided by the at least two modalities, therefore, may be concentrated directly at the teeth, gingival crevices, and teeth crevices.

Further objectives are achieved by providing an oral hygiene system that includes a mouthpiece having at least one arcuate channel and an insert releasably coupled to the arcuate channel, wherein the mouthpiece transmits at least two modalities chosen from a group consisting of a mechanical modality, an iontophoretic modality, and a disinfection modality. The insert is configured to extend and cover the entire length/span of the arcuate channel. The insert comprises two opposing vertical walls mounted to a base wall, creating a substantially U-shaped configuration. Once coupled to the mouthpiece, the insert is adapted to transmit the mechanical modality and the disinfection modality. Further, the releasable attachment feature of the insert provides for quick and easy means of sanitizing the mouthpiece and the components therein. Alternatively, an insert that has been used and "soiled" can be easily detached from the mouthpiece and replaced with a new insert.

For the transmission of the mechanical modality, the insert includes a first set of brush heads attached to one of the vertical walls, a second set of brush heads attached to another of the vertical walls, and a third set of brush heads attached to the base wall, wherein the first, second, and third sets of brush heads project inwardly relative to the U-shaped configuration of the insert. Each brush head comprises a plurality of bristles that is adapted to contact and scrub the surfaces of the teeth (buccal, labial, lingual, occlusal) and gums. In some embodiments, the brush heads are configured to vibrate in multiple axes. In other embodiments, the brush heads are configured to oscillate in one axis. In yet other embodiments, the brush heads are configured to oscillate in a rotational manner. The mechanism for driving the brush heads can be established at a sonic frequency, and thus the brush heads can vibrate at a frequency of less than 20,000 hertz. Alternatively, the brush heads can be driven in an ultrasonic manner at a frequency of 20,000 hertz or higher.

For the transmission of the disinfection modality, the insert includes at least one inlet port disposed in each of the vertical walls, the inlet ports supplying aqueous-based fluid, and preferably disinfecting fluid, to the mouthpiece and thereby irrigating the teeth and gums. In some embodiments, the inlet ports are adapted to spray or release with force the disinfecting fluid. This helps to dislodge food debris and/or breakup plaque buildup. The insert also includes at least one outlet port disposed in the base wall proximate to one of the vertical walls, the outlet port being adapted to remove the disinfecting fluid, food debris, and plaque buildup. In some embodiments, the insert includes at least two outlet ports, one outlet port being positioned at a corner formed between the base wall and one of the vertical walls and another outlet port being positioned at a corner formed between the base wall and the other vertical wall. The outlet ports may be adapted to provide a suction force in order to assist in removing the disinfecting fluid, food debris, and plaque.

The iontophoretic modality comprises at least one electrode positioned in the mouthpiece, wherein the electrode is adapted to contact the gums and apply an electric charge to the teeth. The application of the electric charge depolarizes the adherence bonding of plaque and food debris, and thus loosens and breaks up any buildup of plaque and food debris. It is noted that the electric charge is minor and does not cause any pain to the teeth or gums.

In some embodiments, the mouthpiece includes at least two electrodes for the transmission of the iontophoretic modality. In particular, a first electrode is positioned in the mouthpiece outside the arcuate channel such that it contacts the gums. A second electrode is positioned inside the arcuate channel in a manner such that it does not touch the teeth and gums. The first electrode is adapted to apply an electric charge to the teeth, wherein the electric charge travels from the gums to the teeth as a result of an electric potential generated between the first and second electrodes.

Additional objectives are achieved by providing a hands-free oral hygiene system for cleaning teeth and gums, wherein the system includes a mouthpiece transmitting at least two modalities chosen from a group consisting of a mechanical modality, an iontophoretic modality, and a disinfection modality, as well as a control unit (controller) for controlling the mouthpiece and the transmission of the at least two modalities according to a coordinated sequence. Through the control unit, the system can provide an effective oral treatment wherein the mechanical modality brushes the teeth and gums and dislodges food debris, the iontophoretic modality breaks up plaque and food debris buildup, and the disinfection modality removes the plaque and food debris buildup.

The control unit comprises a control system which monitors and tracks utilization of the oral hygiene and patient care. The control system, in particular, can monitor the time of day and the treatment cycle/session activation. The control system records whether a treatment session was completed or failed to complete, and if failure occurs, it records the particular problem or source of the failure. The control system transmits the above data, through wired or wireless communication technology, to a monitoring system. The control system and monitoring system may be linked to eMAR (electronic Medication Administration Record) utilizing technology, present in hospitals and long term care facilities, to automatically document the administration of medication into certified EHR (electronic health record) technology, using electronic tracking sensors (for example, radio frequency identification (RFID) or electronically readable tagging such as bar coding). As a result, the monitoring system facilitates better compliance with recommended oral hygiene regimens.

The oral hygiene system may further be adapted with a pump unit for transmitting the disinfection modality, such that the pump unit supplies fluid, and preferably disinfecting fluid, to the mouthpiece and removes spent fluid (i.e., disinfecting fluid with food debris and plaque) from the mouthpiece.

Further objectives are achieved by providing a hands-free oral hygiene system that includes a mouthpiece, wherein the mouthpiece has at least one arcuate channel adapted to receive and surround the teeth and gums, and transmits a mechanical modality, an iontophoretic modality, and a disinfection modality in a coordinated sequence. The oral care system provides an easy and effective means of cleaning teeth for people who lack dexterity in their arms and/or hands.

Other objectives of the invention are achieved by providing an oral care system that comprises the hands-free oral hygiene system (e.g., mouthpiece) releasably attached to a housing via an adjustable gooseneck arm. The gooseneck arm holds the mouthpiece at a desired position and orientation relative to the housing, such that a patient, health-care worker or care-taker is not required to hold the mouthpiece in the patient's mouth with hands before, during or after a cleaning session or cycle.

In some embodiments, the housing is a mobile dental cart that is adapted for use in work sites, such as dentist offices, nursing homes, and hospitals. The dental cart provides quick mobility of the oral hygiene system so that it can be moved to/from and used by multiple patients. In other embodiments, the housing is a portable countertop housing that is adapted for personal or home use.

The housing includes at least one socket fitting in which an irrigant bottle containing an irrigation solution (e.g., distilled water, antimicrobial wash, antibacterial wash, fluoride rinse, mouthwash) is inserted and anchored to the housing. For some embodiments, the housing includes three socket fittings for receiving three irrigant bottles, wherein each bottle has a different irrigation solution. Each socket fitting is designed with a lock and key construction using unique shape metrics, for example with respect to male/female threads, projections and/or bayonet mounts, such that only an irrigant bottle having a cap and/or neck with matching or corresponding shape may be inserted. This configuration helps to ensure that a bottle having a particular type of solution is fluidly connected to the appropriate socket fitting and associated fluid lines for proper installation of the oral care system. As one example, a first socket fitting assigned to receive distilled water has a first shape that only accepts a distilled water bottle having a neck with a first corresponding shape, while a second socket fitting assigned to receive fluoride rinse has a second shape that only accepts a fluoride rinse bottle having a neck with a second corresponding shape, and while a third socket fitting assigned to receive antimicrobial wash has a third shape that only accepts an antimicrobial wash bottle having a neck with a third corresponding shape.

The socket fittings with unique shape metrics, in some embodiments, also provide tamperproof protection, so that bottles having unapproved, uncertified irrigant solutions are prohibited from being connected to the oral care system. That is, only bottles containing irrigation solutions certified and approved for use with the oral care system—and more specifically the oral hygiene system (e.g., mouthpiece)—will be allowed to have caps and/or necks with the necessary corresponding shape metrics to connect with the socket fittings. This configuration ensures safety against interchanging irrigant bottles containing unapproved and uncertified solutions.

The oral care system includes a control unit or controller for controlling the oral hygiene system and the application of the modalities (i.e., mechanical modality, an iontophoretic modality, a disinfection modality). The control unit may be processor or processing unit with control system algorithms stored therein, which determine the type of cleaning session (e.g., the type of modalities to be performed, the duration that each modality is applied, the sequence in which the modalities are performed, simultaneous or serial application of modalities) to be given to the patient. The control unit includes an internal storage unit, or alternatively may be connected to a local, external storage unit, to track and save patient information, patient health and dental records, and data concerning the use of the oral care system by the patient(s). The control unit monitors the date and time in which a patient(s) undergoes a cleaning cycle/session. Information regarding whether a cleaning session was completed, interrupted, or failed to complete is recorded. During instances of failure or interruption in the cleaning session, the control unit also records the particular problem and source of the failure. The control unit may be configured to provide patients and users reminders, either an audible reminder or a visual reminder on a display unit, about scheduled cleaning sessions and missed cleaning sessions.

Further, the control unit keeps track of the operational status of the oral care system. If there are issues that affect or potentially affect the proper functioning of the oral care system, the control unit provides warning indicators (e.g., audible or visual). For example, the control unit issues warnings when: (1) the oral hygiene system (i.e., mouthpiece) is connected improperly to the gooseneck arm, or alternatively to inlet and outlet tubes; (2) one or more irrigant bottles are improperly connected to the socket fittings; (3) fluid levels of the irrigation solutions within the bottles are low; (4) when a collection reservoir (for collecting saliva and used irrigation solution evacuated from the mouthpiece) is nearly full; (5) when the pumps (for directing flow of irrigation solutions from the bottles to the mouthpiece and/or for evacuating saliva and used irrigation solutions from the mouthpiece) are malfunctioning; and/or (6) when the power source (e.g., rechargeable battery) powering the oral care system is reaching a low-battery state and requires charging. The control unit maintains a record of system maintenance and notifies the user when the fluid lines in the oral care system require cleaning (e.g., flush fluid lines with cleaning solution) and when the mouthpiece requires cleaning (e.g., cleaning in a separate cleaning device such as an autoclave).

In some embodiments, the control unit is configured to communicate through a network with at least one remote server, transmitting the data that has been tracked and saved by the control unit (e.g., patient information, patient health and dental records, and data concerning the use of the oral care system by the patient) to the server. The server can be any type of patient health record server, such as an electronic Medication Administration Record (eMAR) server. The oral care system includes a wireless transmitter (e.g., Wi-Fi, Bluetooth) so that it can communicate wirelessly with the remote server. Alternatively, the oral care system can connect to the remote server through a wired connection (e.g., Ethernet, fiber-optic cable). The server may be accessible by a patient's doctor, dentist, care-taker, and/or health care provider in order to review the patient's dental health and progress. Through the server, the patient's doctor, dentist, etc. can remotely transmit a text, audio and/or video message to the oral care system, providing the patient or user with recommendations on adjusting future cleaning sessions. In some embodiments, the server provides for the patient's dentist to directly configure the oral care system to perform a prescribed cleaning session, thereby eliminating the need for the patient to manually input the adjustments. This feature of the present invention also helps to prevent incorrect adjustments to cleaning sessions by the user(s). In other embodiments, the connection between the oral care system and the remote server enables live communication between the patient and the patient's doctor, dentist, caretaker, and/or health care provider.

Those skilled in the art will recognize, upon consideration of the above teachings, that the various functions of the control unit may be based upon or performed by the use of one or more hardware components and/or software components executing on computer readable medium(s).

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 12A is a perspective view of an irrigant bottle of the oral care system of FIG. 5.

FIG. 12B is an enlarged view of the neck of the irrigant bottle of FIG. 12A.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
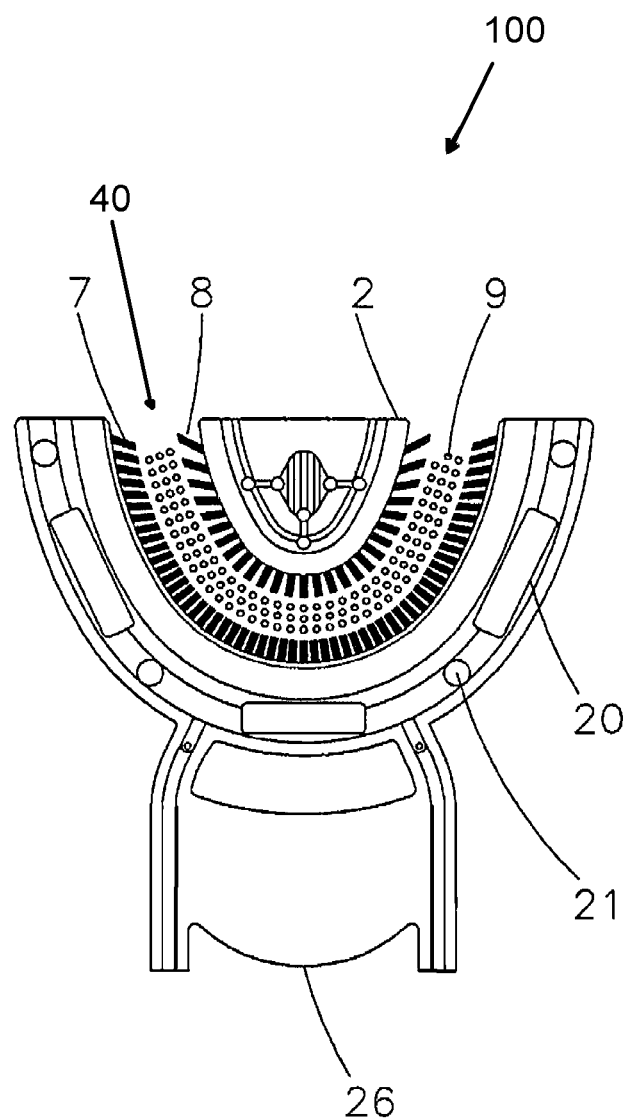
FIG. 1 is a top view of the hands-free oral hygiene system according to an exemplary embodiment of the present invention.
Figure 2:
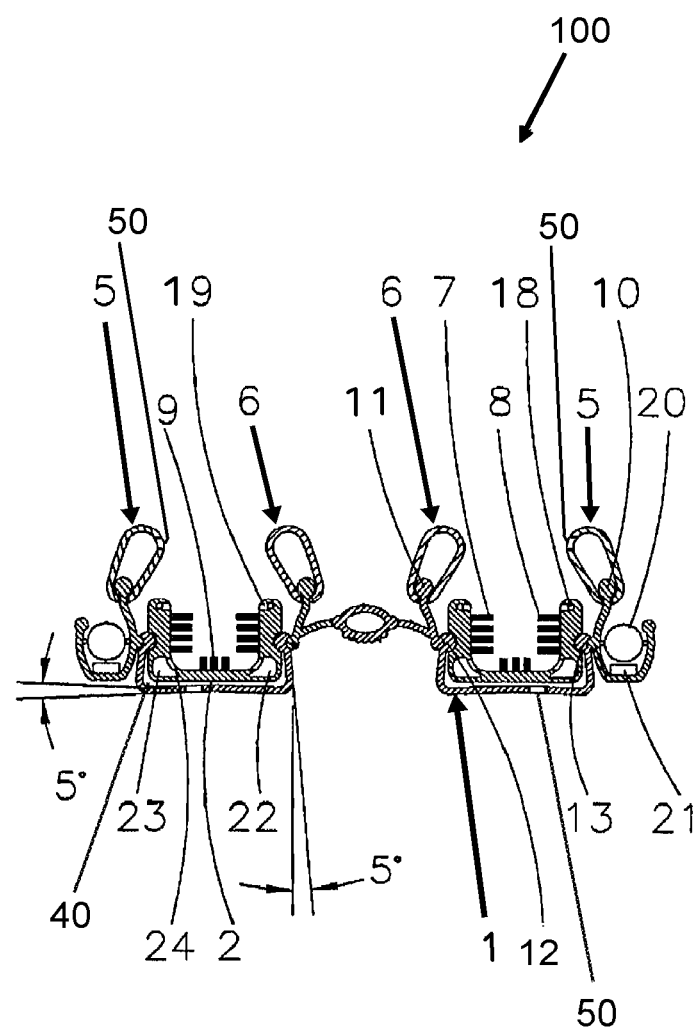
FIG. 2 is a sectional view of the hands-free oral hygiene system of FIG. 1.

Referring to the figures in detail and first to FIGS. 1-2, there is shown an exemplary embodiment of a hands-free oral hygiene system for cleaning teeth and gums. The hands-free oral hygiene system provides effective cleaning of teeth through a device that maintains a stable position within the mouth without being held by a hand, which is especially helpful for people who lack dexterity. FIGS. 1-2 illustrate oral hygiene system 100 formed within the structure of a mouthpiece frame 1. The mouthpiece 1 is elastic and can conform to the shape of a user's oral cavity (i.e., mouth). The mouthpiece 1 may be created using any material that is safe for intraoral contact and has elastic characteristics. For example, the mouthpiece 1 can be made of rubber, polyurethane, or another polymer. The mouthpiece 1 can be designed in any size to accommodate adults and children. In some embodiments, the mouthpiece 1 is customized to a particular user's oral cavity. In other embodiments, the mouthpiece 1 is available is several standard sizes (e.g., XS, S, M, L, XL.)

The mouthpiece 1 includes an arcuate channel 40 that is dimensioned for receiving and surrounding the teeth and gums. As shown in FIG. 2, the arcuate channel 40 of the mouthpiece 1 has a substantially U-shaped cross-section profile.

The mouthpiece 1 further includes two structural rims, an inner rim 6, 11 and an outer rim 5, 10, which extend substantially vertical from the sides of the arcuate channel of the mouthpiece 1. The inner rim 6, 11 is adapted to form a seal with the gums adjacent to the lingual surfaces of the teeth (palatal mucosal seal) while the outer rim 5, 10 is adapted to form a seal with the gums adjacent to the buccal and labial surfaces of the teeth (labial mucosal seal). The combination of the arcuate channel, inner rim, and outer rim form a sealed enclosure or chamber around the teeth and gums such that fluids may not be communicated into or out of the mouthpiece and in particular, the arcuate channel 40. The mouthpiece 1 further includes retro molar pad seals 27 disposed at the ends of the arcuate channel. The pad seals 27 are adapted to contact, conform, and form a seal with the retro molars of the user's mouth, along the maxillae (upper jaw) or mandible (lower jaw). The inner rim 6, 11, outer rim 5, 10 and pad seals 27 are elastic such that they create a spring effect and naturally conform to the user's oral cavity (e.g., gums and retro molars).

The sealed enclosure created by the mouthpiece 1 around the teeth and gums provides a chambering effect which focuses and concentrates the oral care treatment provided by a mechanical modality, disinfection modality and/or an iontophoretic modality (discussed in further detail below). For example, the sealed enclosure provides for effective irrigation of the teeth and gums, by targeting fluid (e.g., disinfecting fluid) towards the teeth and gums, involved in the disinfection modality.

The system 100 further includes an insert 2 (FIGS. 2-3) that releasably couples to the arcuate channel 40 of the mouthpiece 1. The insert 2 is formed by a base wall 30 and two vertical walls 28, 29 (inner wall 29 and outer wall 28) mounted to and extending from opposing sides of the base wall 30. Accordingly, the insert 2 has a substantially U-shaped cross-section configuration. The insert may be made of any material that is safe for intraoral contact. However, unlike the mouthpiece 1, the insert 2 has a rigid structure.

To releasably attach the insert 2 within the arcuate channel, the mouthpiece 1 has at least one fastener disposed at or proximate to the arcuate channel. As shown in FIG. 2, the mouthpiece 1 comprises two fasteners 12, 13 to secure the insert 2 within the arcuate channel. In some embodiments, the fasteners 12, 13 may comprise snap fasteners, wherein the sides of the arcuate channel interlock with the vertical walls of the insert 2. The releasable attachment of the insert 2 with the mouthpiece 1 may be achieved by means of protrusions and recesses designed to fit each other. In one example, the fasteners are formed as one or more protrusions having a circular contour that correspond in shape to one or more recesses formed on the exterior side of the vertical walls of the insert. Once the protrusions are inserted into the recesses, the insert 2 and mouthpiece 1 are firmly connected, thereby inhibiting any movement between the two components.

For the mouthpiece 1 to transmit/provide a mechanical modality, the insert 2 is configured with a plurality of brush heads 7, 8, 9, wherein the brush heads are disposed along the entire length/span of the insert 2. More specifically, the brush heads 7 (lingual brush heads) are mounted on the inner vertical wall 29 of the insert 2 and are adapted to brush the lingual surfaces of the teeth and gums. The brush heads 8 (buccal and labial brush heads) are mounted on the outer vertical wall 28 of the insert 2 and are adapted to brush the buccal and labial surfaces of the teeth and gums. The brush heads 9 (occlusal brush heads) are mounted on the base wall 30 of the insert 2 and are adapted to brush the occlusal surfaces of the teeth. Further, the brush heads 7, 8, 9 are mounted such that they project inwardly with respect to the U-shaped configuration of the insert 2. Each of the brush heads included on the insert 2 comprises a plurality of bristles adapted to contact and brush the surfaces of the teeth and gums.

In some embodiments, the occlusal brush heads 9 are mounted perpendicularly with respect to the base wall 30 of the insert 2. The lingual brush heads 7 and the buccal and labial brush heads 8 may also be mounted perpendicularly relative to the vertical walls 28, 29 of the insert 2. However, in some embodiments, the lingual brush heads 7 and the buccal and labial brush heads 8 may be mounted obliquely or off-perpendicular with the vertical walls 28, 29. For example, the brush heads 7, 8 may be disposed at an angle such that they are partially pointed towards the gum line (e.g., the brush heads are angled away from the base wall of the insert). It is noted that when the bristles of the brush heads become worn, the insert 2 can be detached from the mouthpiece 1 and replaced with a new insert 2 having fresh (un-worn) brush heads. This feature allows for easy cleaning and maintenance of the oral hygiene system.

The mechanical modality further comprises at least one vibration device or actuator 20 disposed in the mouthpiece 1, wherein the actuator 20 is adapted to vibrate the brush heads 7, 8, 9 at sonic (e.g., less than 20,000 hertz) and/or ultrasonic frequencies (more than 20,000 hertz). The actuator 20, for example, may be a piezoelectric actuator, a micro-actuator, or nano-actuator. In some embodiments, the brush heads are adapted to vibrate in multiple axes. In other embodiments, the brush heads are configured to oscillate in one axis. In yet other embodiments, the brush heads are configured to oscillate in a rotational manner. By vibrating and/or oscillating the brush heads against the surfaces of the teeth and gums, the mechanical modality is able to scrub and clean the teeth as well as dislodge any food debris that may have accumulated between the teeth or within the gingival crevices.

The one or more actuators 20 are configurable such that bristle action can be driven at different frequencies between one treatment session (teeth cleaning) and a subsequent treatment session. The actuators can also vary (i.e., increasing and/or decreasing) the driving frequency within a single treatment session. For example, the actuators will initially vibrate the brush heads at a first frequency within the sonic region and then gradually increase the magnitude to a second frequency within the ultrasonic region. If the mouthpiece 1 has multiple actuators 20, the actuators can drive their respective brush heads at the same frequency or at different frequencies in a single treatment session. This characteristic of varying the driving frequency of the actuators helps to provide beneficial oral care customized to a particular user's oral health.

As shown in FIG. 1, the mouthpiece 1 has three actuators 20, wherein each actuator drives bristle action—using sonic or ultrasonic waves—for one of the brush head sets. However, the mouthpiece in some embodiments may be designed with one or two actuators. Where there is only one actuator, the brush heads 7, 8, 9 are collectively driven at the same frequency. In the embodiments where two actuators are included in the mouthpiece, different combinations of the brush heads 7, 8, 9 may be driven by the two actuators. One arrangement may comprise a first actuator driving the lingual brush heads 7 and the buccal and labial brush heads 8 and a second actuator driving the occlusal brush heads 9. Other arrangements of the two actuators and three sets of brush heads are possible. In further embodiments, the mouthpiece may have more than three actuators, which allows for subsets of the brush heads 7, 8 and/or 9 to be driven at different frequencies. For example, where four actuators are provided, two of the actuators may be assigned to the lingual brush heads 7, such that one actuator drives a subset of brush heads 7 aligned with the user's incisors and canine teeth while another actuator drives a subset of brush heads 7 aligned with the user's premolar and molar teeth. This feature is beneficial for user's who have sensitive teeth, as the actuators can be configured to provide low frequency vibrations to the brush heads that are aligned with the specific sensitive teeth. Alternatively, if certain teeth require extensive cleaning, the actuators can be configured to provide high frequency (e.g., ultrasonic) vibrations to the brush heads that are aligned with those teeth.

With regard to the disinfection modality, an aqueous-based disinfecting fluid, such as an antiseptic mouthwash, is provided via the insert 2 within the sealed enclosure of mouthpiece 1 to irrigate the teeth and gums and remove any food debris and plaque buildup. Further, the disinfecting fluid is adapted to kill bacteria present on the teeth and gums and/or apply a chemical layer (e.g., fluoride) to protect against tooth decay and gingivitis. The insert 2 has at least one inlet port 19 disposed in each of the vertical walls and at least one outlet port 24 disposed in the base wall proximate to one of the vertical walls (e.g., corner of insert 2 having a U-shaped configuration). The inlet ports 19 supplies disinfecting fluid to the teeth and gums while the outlet port 24 is adapted to discharge and remove the "spent" disinfecting fluid as well as food debris and plaque buildup. In the embodiment shown in FIG. 2, the insert 2 includes two inlet ports 19 and two outlet ports 24. One inlet port and one outlet port have openings that are directed substantially towards the lingual surfaces of the teeth. The other inlet port and outlet port have openings that are directed substantially towards the buccal/labial surfaces of the teeth. It is noted that reference to one inlet port or one outlet port may encompass a set of inlet ports or a set of outlet ports distributed along the span of the insert 2. Accordingly, there may be multiple locations along the insert 2 where disinfecting fluid is supplied into the sealed enclosure of the mouthpiece 1 and multiple locations along the insert 2 where spent fluid, food debris, and plaque are removed.

Figure 3:
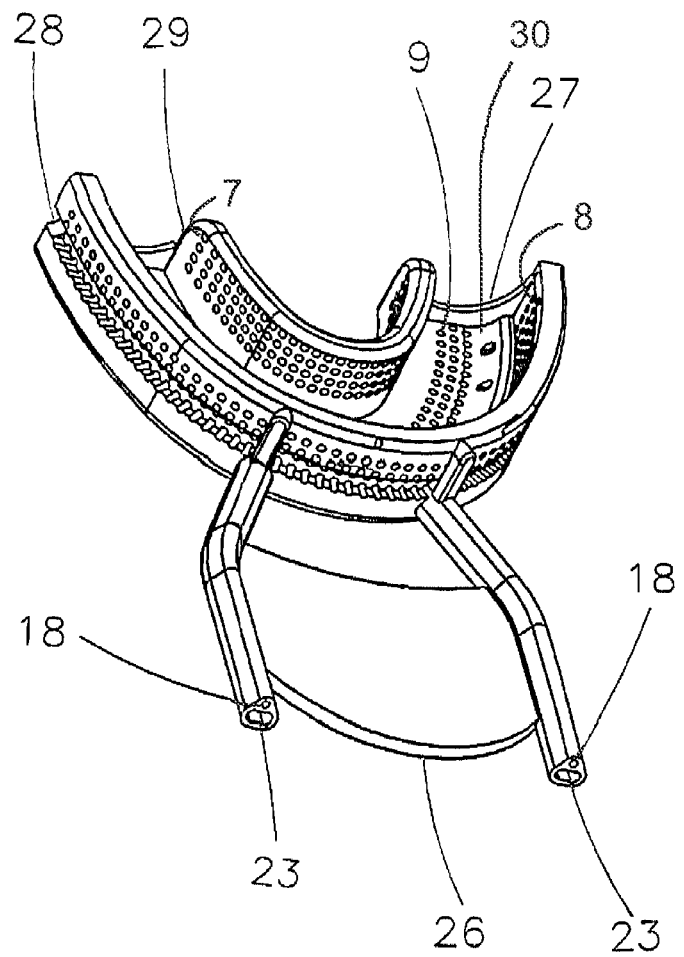
FIG. 3 is a perspective view of the hands-free oral hygiene system of FIG. 1.

The insert 2 also comprises at least one supply channel 18 in fluid communication with the inlet ports 19 and at least one discharge channel 22, 23 in fluid communication with the outlet ports 24. The supply channel 18 is adapted to feed the disinfecting fluid to the inlet ports 19 from a supply unit, which stores the disinfecting fluid. The discharge channel 22, 23 is adapted to discharge and remove spent fluid, food debris, and plaque from the outlet ports to a drain unit, such as a sink or fluid collection device. As shown in FIGS. 2-3, the insert 2 has two supply channels 18 and two discharge channels 23 for circulating disinfecting fluid through the mouthpiece 1.

In some embodiments, the inlet ports 19 are adapted to spray, eject and release with force the disinfecting fluid. This feature of the inlet ports helps to thoroughly irrigate the teeth and gums as well as dislodge any food debris or plague buildup. In some embodiments, the outlet ports 24 are adapted to provide a suction force in order to assist in removing the spent disinfecting fluid, food debris, and plaque buildup. The suction force provided ensures that fluid, food debris, and plaque are removed continuously and reduces the likelihood that outlet ports 24 and discharge channels 22, 23 will be obstructed with food debris and plaque.

In some embodiments, the oral hygiene system 100 includes a pump unit for communicating the disinfecting fluid from a supply unit, to and through the mouthpiece 1, and to a drain unit. In particular, the pump unit provides the ejection and suction capabilities of the inlet and outlet ports, respectively.

Figure 4:
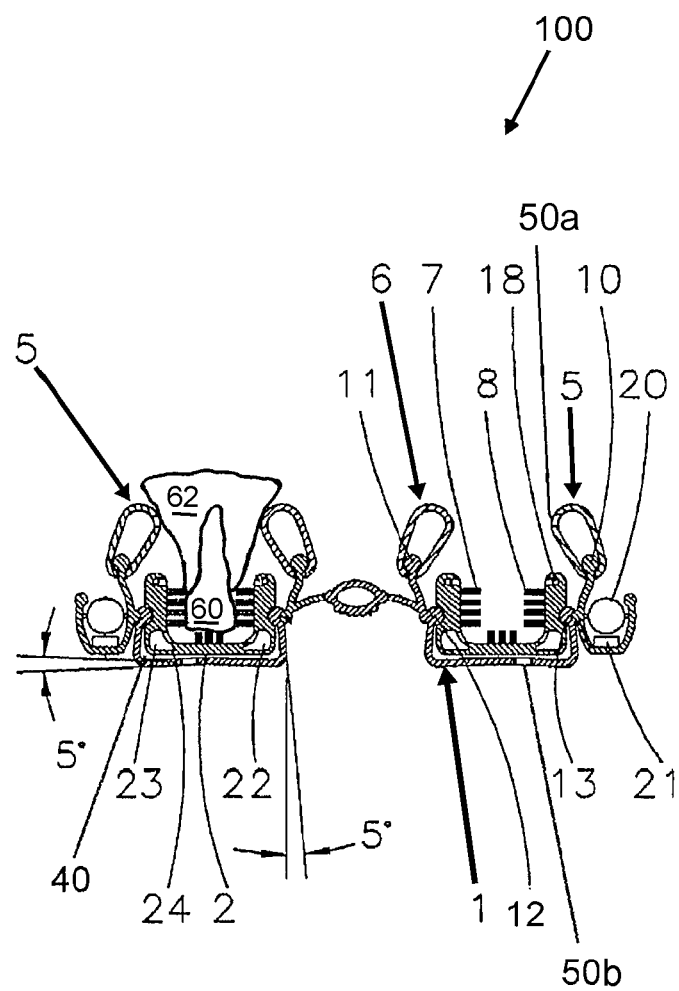
FIG. 4 is a sectional view of the hands-free oral hygiene system of FIG. 1 with teeth and gums positioned therein.

The iontophoretic modality comprises at least one electrode 50 positioned in the mouthpiece, wherein the electrode is adapted to contact the gums 62 (FIG. 4). In some embodiments, the electrode 50 may be positioned along one of the structural rims (inner rim 6, 11; outer rim 5, 10). With the electrode 50 being in contact with the gums 62, the electrode is adapted to apply an electrical charge to the teeth 60. The application of an electrical charge depolarizes the adherence bonding of plaque and food debris on the teeth, and thus loosens and breaks up any buildup of plaque and food debris. It is noted that the electric charge is minor and does not cause any pain to the teeth or gums of the user.

In some embodiments, the mouthpiece 1 includes at least two electrodes 50 for the transmission of the iontophoretic modality. In particular, as shown in FIG. 4, a first electrode 50a is positioned in the mouthpiece outside the arcuate channel such that it contacts the gums 62, i.e., disposed on one of the structural rims (e.g., outer rim 5, 10). Conversely, a second electrode 50b is positioned inside the arcuate channel in a manner such that it does not touch the teeth 60 and gums 62. For example, the second electrode 50b may be disposed within the arcuate channel of the mouthpiece 1 substantially adjacent to and under the base wall of the insert 2. The first electrode is adapted to apply an electric charge to the teeth, wherein the electric charge travels from the gums to the teeth as a result of an electric potential generated between the first and second electrodes.

With the iontophoretic modality loosening and breaking up the plaque and food debris that has accumulated on the teeth and gums, a comprehensive and synergistic oral care treatment is provided when combined with the mechanical and/or disinfection modalities.

In order to provide energy for the at least one actuator 20 to vibrate the brush heads and for the at least one electrodes to provide an electric charge, the oral hygiene system includes at least one power source 21 disposed in the mouthpiece 1. In some embodiments, the power source 21 comprises a 3V battery. In other embodiments, the power source 21 comprises a lithium cell. Regardless of the type of battery used, the power source 21 maintains a small profile and does not increase the size the mouthpiece 1 substantially. In some embodiments, power is supplied to the actuators and electrodes from an external power source, such as an electrical outlet, via an electric cable connected to the mouthpiece. Additionally, the external power source may be used to recharge the power source 21.

As shown in FIG. 1, the mouthpiece 1 generally has a parabolic profile resembling a row of teeth. The oral hygiene system 100 includes an armature platform 26, which extends out from the curved or convex side of the mouthpiece 1. More specifically, the armature platform 26 is positioned at and proximate to the vertex of the curved side of the mouthpiece. The platform 26 serves as a handle for a person (e.g., caregiver) to easily insert the mouthpiece 1 into an oral cavity or mouth. In some embodiments, the armature platform 26 provides support for the supply channels and discharge channels that are connected to a supply unit and drain unit, respectively.

In some embodiments of the hands-free oral hygiene system, the system includes the mouthpiece 1 for transmitting at least two modalities chosen from the group consisting of the mechanical modality, the iontophoretic modality, and the disinfection modality, and a control unit for controlling the mouthpiece 1 and the transmission of the at least two modalities according to a coordinated sequence. Via the control unit, a user is able to adjust and program which modalities to transmit, the sequence of transmission, and the length of time for transmitting a modality. In some embodiments, the control unit can be programmed so that the modalities are transmitted simultaneously. In other embodiments, the modalities may be transmitted sequentially. In still other embodiments, the modalities may be transmitted by a combination of simultaneous and sequential coordination. The control unit also provides means for configuring the actuators with respect to drive frequencies. Through the control unit, the user is able to establish whether the actuators maintain a constant drive frequency or vary drive frequency in a single treatment session.

The control unit is also adapted to record and track utilization of the oral hygiene system. For example, the control unit tracks when and how many times the system is turned on and off. It keeps track of whether the system is initialized and/or configured prior to a treatment session being provided to a person. In some embodiments, the control system is linked to sensors (e.g., pressure, temperature) positioned on the mouthpiece 1 to detect when the mouthpiece has been inserted into a person's mouth and the person is biting down on the mouthpiece. Information concerning the status of each component of the oral hygiene system is further collected by the control system in order to determine whether maintenance (e.g., equipment sterilization, equipment replacement, fluid refill) is required. For example, the control system may detect when a particular insert 2 needs to be replaced because the brush heads are worn and no longer provide effective brushing of the teeth. As another example, the control unit can monitor the fluid levels of a drain unit (e.g., fluid collection device) that is connected to the mouthpiece, thereby providing an indication or warning when the drain unit is almost full and needs to be emptied. In similar respect, the control unit can monitor the fluid levels of a supply unit (for providing disinfecting fluid) that is connected to the mouthpiece. The control system can also monitor pressure levels to determine whether fluid communication into, through, and out of the mouthpiece is laminar as well as detect if there are any obstructions at or near the inlet ports 19 and outlet ports 24 of the insert 2. If the control system recognizes that the ports are blocked, a warning signal or indication is provided. Additionally, the control system provides feedback on the status of connections between various components of the oral hygiene system. The control system detects whether the insert 2 has been properly positioned within the arcuate channel 40 of the mouthpiece 1. If the insert 2 and the mouthpiece 1 are misaligned, the control system provides an indication that the two components need to be repositioned to achieve alignment. The control system checks whether the connections between the at least one supply channel 18 and a supply unit (for supplying disinfecting fluid), between the discharge channels 22, 23 and a drain unit, and between a pump unit, the channels, the supply unit, and the drain unit are secure; if any loose connections are detected the control system will provide an appropriate warning signal and, in some cases, prevent the oral hygiene system from being engaged and providing treatment until after the issues/problems have been resolved.

In some embodiments, the control unit or system detects and registers whether a treatment cycle/session completed successfully or failed due to a problem. If the treatment session was interrupted or prematurely terminated for technical issues, the control unit gathers information regarding the particular component(s) of the oral hygiene system that are involved in the technical issue and provides assistance in diagnosing and resolving the issue. The control unit also gathers information pertaining to when (during what portion the treatment session) the technical issue occurred and how much of the treatment session was performed before termination. For example, if the disinfecting fluid supply unit or reservoir goes empty during a treatment session, the control unit will signal that the session failed and communicate which modality(ies) was being transmitted when the error occurred. The information concerning utilization and completed/failed treatment cycles is then transmitted—wirelessly or through wired communication lines—to a monitoring system. Through the monitoring system, a person (e.g., medical staff, assisted living staff, caregiver) can monitor and evaluate a patient's treatment and overall oral health, including when (e.g., time of day) a treatment session is activated. The control system and monitoring system may be linked to eMAR (electronic Medication Administration Record) utilizing technology, present in hospitals and long term care facilities, to automatically document the administration of medication into certified EHR (electronic health record) technology, using electronic tracking sensors (for example, radio frequency identification (RFID) or electronically readable tagging such as bar coding). As a result, the monitoring system in combination with eMAR facilitates better compliance with recommended oral hygiene regimens. Further, through the monitoring system, medical staff (i.e., dentist), assisted living staff, or caregivers can review a patient's oral care treatment with particular emphasis with compliance to oral hygiene regimens.

In yet other embodiments of the hands-free oral hygiene system, the mouthpiece 1 transmits all three modalities—mechanical modality, the iontophoretic modality, and the disinfection modality—in a coordinated sequence (e.g., simultaneous, sequentially, or combination thereof).

One skilled in the art will understand, in view of the foregoing description, that the hands-free oral hygiene system may be implemented with two of the mouthpieces so that oral care is provided to both the upper teeth and the lower teeth at the same time. In particular, one mouthpiece may be attached to, or placed adjacent to, another mouthpiece in a back-to-back configuration. Each such mouthpiece is adapted to transmit at least two modalities chosen from the group consisting of the mechanical modality, the iontophoretic modality, and the disinfection modality. Both mouthpieces may be configured to provide the same type of cleaning treatment to both upper and lower teeth, or alternatively, each mouthpiece may be independently configured to provide different types of cleaning treatment for the upper and lower teeth.

Figure 5:
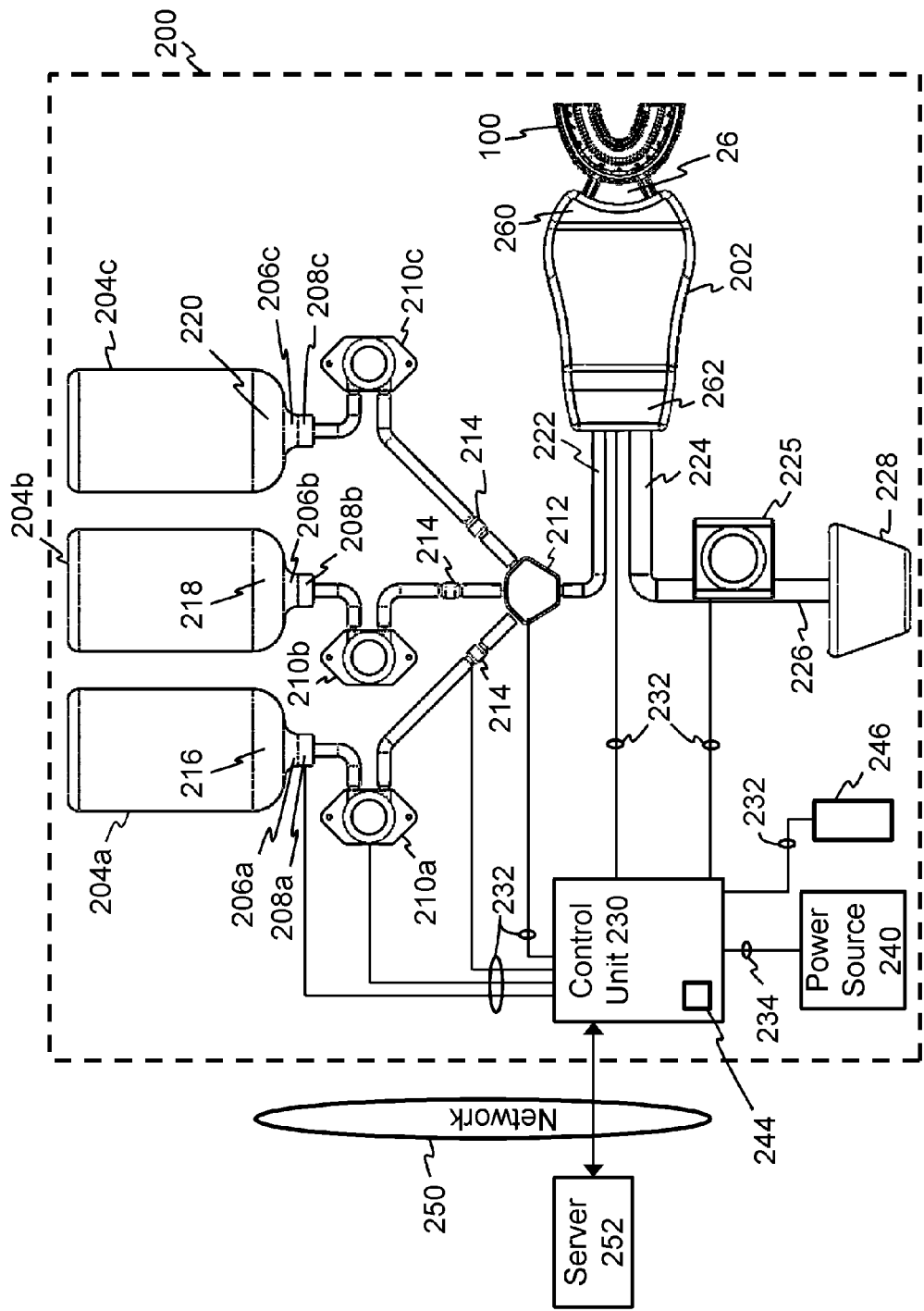
FIG. 5 is a schematic view of an oral care system implemented with the hands-free oral hygiene unit shown in FIGS. 1-4.

FIG. 5 shows an embodiment of an oral care system 200 comprising a housing (e.g., mobile dental cart 270 in FIGS. 6-8; portable countertop housing 280 in FIGS. 9-11), an adjustable gooseneck arm 202 attached to the housing, and the oral hygiene system 100 connected to the gooseneck arm 202. The oral care system enables hands-free cleaning of teeth, which is beneficial for people who lack dexterity. The gooseneck arm 202 includes a mouthpiece coupler 260 which releasably connects to the oral hygiene system 100 by coupling to the armature platform 26 of the oral hygiene system. At an opposite end of the gooseneck arm, there is an arm coupler 262 for releasably attaching the gooseneck arm 202 to the housing. The detachable mechanism of the couplers provides for replacement of an old oral hygiene system with a new/clean oral hygiene system, or alternative, enables an old oral hygiene system to be separated, cleaned in an instrument cleaning machine (e.g., autoclave), and thereafter reinstalled with the oral care system.

The gooseneck arm 202 is configured to constantly hold the oral hygiene system 100 at a desired position and orientation (defined by the patient or care-taker) relative to the housing for easy insertion into the patient's mouth. The gooseneck arm maintains the desired position without any intervention from the patient or care-taker, such that the patient and care-taker are not required to hold the oral hygiene system 100 (e.g., mouthpiece 1) in the patient's mouth with hands before, during or after a cleaning session. This feature of the present invention is beneficial because the gooseneck arm reduces the likelihood that the oral hygiene system 100 accidentally drops on the floor or touches other contaminated surfaces. The gooseneck is also beneficial for people who are handicapped or lack dexterity in performing tasks with their hands. Once the gooseneck arm is adjusted—for example, by a care-taker—so that the oral mouthpiece 1 is at a position and orientation favorable for easy insertion into the mouth for an initial cleaning session, the handicapped person does not require the assistance of the care-taker to place the mouthpiece in his/her mouth for subsequent cleaning sessions.

The gooseneck arm 202 is adjustable and self-supporting such that its positioning can be changed in order to reposition the oral hygiene system 100 according to the patient's or the care-taker's preference. The gooseneck arm is sufficiently flexible to be bent into a variety of different shapes and orientations simply by bending it. Further, the gooseneck arm is sufficiently resilient to hold its shape after it has been adjusted into a desired shape and orientation. Accordingly, the mouthpiece 1 of the oral hygiene system 100 may be precisely positioned for easy insertion into the mouth simply by bending the gooseneck arm 202 and without touching any part of the oral hygiene system 100.

Upon coupling the gooseneck arm to the housing via the arm coupler 262 and the oral hygiene system to the gooseneck arm via the mouthpiece coupler 260, the at least one supply channel 18 is fluidly connected to a inlet flow line 222 disposed in the housing for supplying irrigation solutions 216, 218, 220 from irrigant bottles 204 to the inlet ports 19 of the oral hygiene system 100. Additionally, after the housing, gooseneck arm, and oral hygiene system are connected to each other, the at least one discharge channel 22,23 is fluidly connected to an outlet flow line 224 for removing saliva and spent irrigation solution from the oral hygiene system 100.

To produce fluid flow to the mouthpiece 1 of the oral hygiene system 100 through the inlet flow line 222, the oral care system 200 comprises at least one irrigation pump 210 disposed in the housing. For some embodiments, there is one irrigation pump 210 to propel irrigation solution(s) from one or more irrigant bottles 204, through the inlet flow line 222, and into the at least one supply channel 18 of the oral hygiene system 100. FIG. 5, in particular, shows an embodiment where the oral care system has three irrigation pumps 210a, 210b, 210c to independently move different irrigation solutions to the oral hygiene system. That is, the irrigation pump 210a directs an irrigation fluid 216 contained in the irrigant bottle 204a to a control valve 212 before entering into the inlet flow line 222; the irrigation pump 210b directs an irrigation fluid 218 contained in the irrigant bottle 204b to the control valve 212 before entering into the inlet flow line 222; and the irrigation pump 210c directs an irrigation fluid 220 contained in the irrigant bottle 204c to the control valve 212 before entering into the inlet flow line 222.

The control valve 212, disposed within the housing, controls which irrigation solution is fed into the inlet flow line 222. In some embodiments, the control valve 212 is configured to provide flow from only one of the irrigation pumps at any given movement. Alternatively, the control valve provides for flow from at least two irrigation pumps. As such, two or more different irrigation solutions can be propelled simultaneously through the inlet flow line 222. Such a configuration may be beneficial in providing a synergistic effect of the combined irrigation solutions during application of the disinfection modality. The control valve 212 is also adapted to control the flow and pressure with which the irrigation solution(s) is transmitted to the oral hygiene system 100.

The oral care system 200 may also include check valves 214 positioned downstream from each irrigation pump 210 and upstream of the control valve 212, within the housing. The check valves allow flow in only one direction (i.e., towards the control valve), thereby preventing backflow (of backwash fluids) into the irrigation pumps and irrigant bottles. In addition, the check valves 212 protect the irrigation pumps against potential cross-contamination. In some embodiments, the check valves 212 may be further adapted to plug flow in both directions, creating complete blockage of the flow line.

To remove the saliva and spent irrigation solutions—as well as any solid objects removed from the patient's teeth during the cleaning process—from the oral hygiene system 100 through the outlet flow line 224, an evacuation pump 225 is used. The evacuation pump 225 within the housing provides a suction force in the outlet flow line 224, which is translated to the discharge channels 22, 23 and the outlet ports 24 of the oral hygiene system 100. After the saliva and spent irrigation solutions are removed from the mouthpiece 1 of the oral hygiene system 100, they are transferred to a drain hose 226. The drain hose 226, in some embodiments, is connected to a collection reservoir 228 which collects the saliva and spent irrigation solutions. Once the collection reservoir 228 is nearly full, it can be detached from the drain hose 226, removed from within the housing, and its contents emptied into a drain or sink. Thereafter, the collection reservoir may be cleaned and reinstalled into the housing. The collection reservoir 228 may be a flask of any size, for example a 250 mL or 500 mL flask. In alternative embodiments, the drain hose 226 extends outside the housing so that the distal end of the drain hose may be positioned directly into a drain or sink (see FIGS. 9-10).

The oral care system 200 further comprises one or more socket fittings 208 disposed along the exterior surface 272, 282 of the housing (FIGS. 6-11). As shown in FIG. 5, the oral care system 200 has three socket fittings 208a, 208b, 208c adapted to receive the closure caps, necks and/or spouts 206a, 206b, 206c of irrigant bottles 204a, 204b, 204c respectively. Each bottle 204a, 204b, 204c contains a different type of irrigation solution 216, 218, 220 (e.g., distilled water, antimicrobial wash, antibacterial wash, fluoride rinse, oxygenating mouthwash, liquid dentifrice). Once the closure caps, necks and/or spouts 206 are connected to the socket fittings 208, fluid communication is created between the irrigant bottles and the irrigation pumps 210. In some embodiments, the socket fitting 208 is a female component while the closure cap and neck form a male component. Alternatively, the socket fitting 208 may be the male component while the closure cap and neck form the female component. Upon connecting the closure caps, necks and/or spouts to the socket fittings, a fluid-tight seal is formed, thereby preventing leakage of irrigation solution. For example, the socket fitting may include a gasket, stopper or o-ring which is compressed when the closure cap, neck and/or spout 206 is mated with the socket fitting 208.

The socket fittings 208 have a lock and key design, wherein each socket fitting has unique shape metrics with respect to its female/male threading, projections, and/or bayonet mounts. Given the lock and key configuration, the socket fitting only allows mating with an irrigant bottle having a closure cap, neck and/or spout defined by a shape complementary to that of the socket fitting. This feature helps to protect the oral care system 200 by ensuring that a bottle having a particular type of solution is fluidly connected to the appropriate socket fitting and associated fluid lines, thereby providing proper installation of the oral care system. As one example, socket fitting 208a—assigned to receive distilled water 216—has a first shape that only accepts a distilled water bottle 204a having a closure cap, neck and/or spout 206a with a first complementary shape. Socket fitting 208b—assigned to receive fluoride rinse 218—has a second shape that only accepts a fluoride rinse bottle 204b having a closure cap, neck and/or spout 206b with a second complementary shape. Third socket fitting 208c—assigned to receive antimicrobial wash 220—has a third shape that only accepts an antimicrobial wash bottle 204c having a closure cap, neck and/or spout 206c with a third complementary shape.

The socket fittings 208, each with their unique shape metrics, provide tamperproof protection. Specifically, only irrigation solutions which have been certified and approved for use with the oral care system 200 are allowed to be stored in the irrigation bottles having the necessary closure caps, necks and/or spouts that fit into the socket fittings 208. Thus, the lock and key design of the socket fittings with their unique shape metrics ensures that irrigant bottles having unapproved and uncertified irrigation solutions cannot be connected to the oral care system.

FIGS. 12A-12B show one embodiment of the irrigant bottle 204 having a triangular shape (i.e., prism with triangular cross section). For example, the irrigant bottle may be formed in the shape of an isosceles triangle. The closure cap, neck and/or spout 206 similarly have a triangular shape, which complements the unique shape metrics of the lock and key design of the socket fittings 208. That is, one or more of the socket fittings 208 may have a triangular shaped opening adapted for receiving the closure cap, neck and/or spout of the irrigant bottle shown in FIGS. 12A-12B. The top 207 of the closure cap, neck and/or spout 206 may further be slanted or beveled (FIG. 12B). The slanted top 207 of the cap, neck and/or spout helps with connecting the irrigant bottle in an appropriate position within the socket fitting. In some embodiments, the slanted top 207 must also correspond with a complementary slanted portion of the socket fitting in order to connect the irrigant bottle. Thus, the beveled shape of the top 207 not only helps to confirm the position of the irrigant bottle in the socket fitting but also verifies that an approved bottle is being connected to the oral care system. The irrigant bottle and the closure cap, neck and/or spout may be characterized by other shapes or combinations of shapes, including cylindrical, cubic, rectangular, or polygonal shapes. For example, as shown in FIGS. 5-11, the irrigant bottle as well as the closure cap, neck and/or spout are cylindrical.

Alternatively or in addition to the lock and key design of the socket fittings, the oral care system may also include one or more RFID (radio frequency identification) sensors to identify and track electronic coding tags placed on the irrigant bottles. The RFID sensor(s) will detect whether an appropriate irrigant bottle having a valid identification tag is being inserted into a socket fitting. If the RFID sensor(s) detect an invalid tag, the socket fitting 208 will inhibit physical connection of the irrigant bottle 204 and/or prevent any communication of fluid from the irrigant bottle 204 to the irrigation pump 210, control valve 212, inlet flow line 222, and oral hygiene system 100. The one or more RFID sensors may be positioned proximate to or at the socket fittings 208. However, given the wireless range of RFID technology, the sensors may be positioned anywhere within the housing of the oral care system 200.

Referring back to FIG. 5, in some embodiments, the closure cap, neck and/or spout 206 of each irrigant bottle has a center which is initially closed by a slidable plug. The socket fitting 208 has in its center a tap mechanism which engages the slidable plug when the closure cap, neck and/or spout 206 is inserted into the fitting 208. When engagement is achieved, the tap mechanism contacts the slidable plug, pushing the plug away from the surface of the closure cap to permit the irrigation solution contained within the bottle to be dispensed into the oral care system. When the irrigant bottle is released from the socket fitting 208, the slidable plug automatically returns to a position flush with the closure cap (for example, by means of a spring mechanism disposed within the neck of the bottle). Alternatively, or in addition, the tap mechanism pulls the slidable plug back into its initial position flush with the closure cap surface as the irrigant bottle is removed from the socket fitting 208 (for example, by magnetic contact between the slidable plug and the tap mechanism). This configuration of the closure cap, neck and spout with slidable plug prevents any irrigation solution contained in the bottle from spilling out when the bottle is disposed in an inverted position, as shown in FIGS. 5-11.

In other embodiments, the closure cap 206 may be a cover or membrane which closes the spout of the bottle 204 and provides a fluid-tight seal. The cover or membrane prevents spillage of irrigation solution when the bottle 204 is inverted (i.e., spout oriented in a downward direction) and installed into the socket fitting 208. Once the irrigant bottle is installed, the socket fitting has a hypodermic needle-type mechanism which extracts the irrigation solution. Specifically, the hypodermic needle is disposed in a recessed position within the socket fitting when no bottle is installed in the socket fitting. Once the socket fitting detects that a certified/approved irrigant bottle is placed therein, for example by means of one or more pressure, laser, ultrasonic and/or RFID sensors in the socket fitting, the hypodermic needle is extended out of its recessed position. As the hypodermic needle is extended, its beveled tip punctures the cover or membrane, thereby creating access to the irrigation solution contained within the irrigant bottle. The irrigation pump 210 can assist in drawing out the irrigation solution through the hypodermic needle. Once the closure cap, neck and spout are removed from the socket fitting, the hypodermic needle is retracted safely back into its recessed position. The cover or membrane may be composed of a polymer (e.g., silicone), elastomer, or plastic. In some embodiments, the cover or membrane is a self-sealing septum, which allows for multiple punctures by the hypodermic needles. This feature allows for an irrigant bottle to be reused and refilled with irrigation solution and installed into the oral care system multiple times.

In still other embodiments, the closure cap 206 may be a rupturable cover or membrane which can be manually removed or broken before the irrigant bottle is installed into the socket fitting. Other types of closure mechanisms which accomplish the same purpose (i.e., clean installation of the irrigant bottle into socket fitting without spillage of irrigation solution) may be incorporated into the oral care system 200.

As shown in FIG. 5, the oral care system 200 also includes a control unit 230 for controlling the functions and operation of the oral hygiene system 100, pumps 210, 225 and the valves 212, 214. Disposed within the housing, the control unit 230 may be in the form of a processor, microprocessor, or some other processing unit (e.g., including hardware and software elements) that is communicatively connected with other components of the oral care system 200 via communication lines 232. For example, the control unit 230 transmits control signals through the communication lines 232 to the irrigation pumps 210 to turn the pumps on/off and control the flow, pressure and quantity of fluid propelled to the control valve 212 and into the inlet flow line 222 (note, for simplicity, FIG. 5 only shows the pump 210a connected to the control unit 230). The irrigation pumps 210 also provide feedback to the control unit 230 regarding status of the pumps. The control unit is also connected to the check valves 214 and the control valve 212. Upon receiving control signals from the control unit 230, the control valve 212 determines which flow line(s) to open and close and thus which irrigation solution(s) is transferred into the inlet flow line 222 and ultimately to the oral hygiene system 100. The control unit 230 also adjusts the flow and pressure by controlling the size of the opening provided. In similar respect to the irrigation pumps, the control unit 230 can control the evacuation pump 225. The magnitude of the suction force generated by the evacuation pump can be adjusted through the control unit. The control unit can turn on/off the evacuation pump based on a time cycle. In some embodiments, with one or more fluid level sensors (e.g., ultrasonic liquid level sensor, capacitive fluid level sensor) disposed in the oral hygiene system 100 (i.e., in any part of the oral hygiene system 100), the control unit 230 can detect the fluid volume of saliva and spent irrigation fluid in the patient's mouth and initiate the evacuation pump when a defined maximum threshold is met. Conversely, if the fluid volume drops below a defined minimum threshold, the control unit 230 powers down the evacuation pump 225.

The oral hygiene system 100 is also controlled by the control unit 230 via a communication line 232 which is feed through the gooseneck arm 202. When the oral hygiene system 100 is coupled to the gooseneck arm, the communication line 232 is connected to one or more signal lines disposed within the oral hygiene system 100. As a result, direct communication between the control unit 230 and the actuators 20, electrodes 50, inlet ports 19, and outlet port 24 of the oral hygiene system 100 is created, which provides for the control unit to configure and control operation of the oral hygiene system. The control unit determines which modalities (i.e., mechanical modality, iontophoretic modality, disinfection modality) are to be performed in a given cleaning session and the time duration of each modality. The control unit can be used to set the total duration of the cleaning session. In some embodiments, a cleaning session lasts two minutes. In other embodiments, the cleaning session can be set to less than two minutes, such as 90 seconds. The control unit 230 can configure the oral hygiene system to apply the modalities in serial order, parallel (simultaneously) or a combination thereof. The exact order in which the modalities are performed serially and the particular modalities that are performed simultaneously are managed through the control unit. Accordingly, the control unit 230 can send control signals to the actuators 20 in order to initiate or terminate vibrations of the brush heads 7, 8, 9 and adjust the frequency of the vibrations. Similarly, the control unit can send control signals to the electrodes 50 in order to initiate or terminate transmission of electrical charge to the patient's teeth.

In some embodiments, the control unit 230 may be configured to start a cleaning session once a patient bites onto and closes his/her mouth around the oral hygiene system 100 (e.g., mouthpiece 1). For example, one or more sensors (e.g., pressure sensors) may be installed in the oral hygiene system 100—along any portion of the mouthpiece 1 and/or insert 2—to detect pressure applied by the patient's teeth. The sensor(s) then sends signals to the control unit 230 to indicate when pressure is detected and to begin a cleaning session. Conversely, if the patient opens his/her mouth and ceases to bite on the oral hygiene system 100, the sensor(s) detects a reduction in pressure, at which point the control unit 230 reacts by pausing or terminating the cleaning session. The oral care system may be configured so that the control unit immediately initiates a cleaning session upon detecting pressure in the oral hygiene unit. Alternatively, there may be a delayed response (e.g., delay of 1, 2 or 3 seconds) between the detection of pressure and the start of the cleaning session.

The control unit 230 also monitors the fluid levels of the irrigant bottles 204 using sensors installed in the socket fittings 208. Once the control unit detects that the irrigation solution within a particular irrigant bottle drops below a defined level (or if a certain amount of fluid has passed through the socket fitting), a warning indicator—audible and/or visual—is provided to inform the patient and/or care-taker that a replacement bottle is needed. As an example, if the volume of irrigation solution is less than ¼ of the volume of the irrigant bottle, then the control unit issues a warning indicator.

In some embodiments, the control unit 230 also monitors the fluid level of the collection reservoir using a sensor. If the control unit detects that the contents (e.g., salvia and spent irrigation solutions) within the collection reservoir rises above a defined level, a warning indicator—audible and/or visual—is provided to signal that the collection reservoir needs to be emptied in the near future. For example, if the volume of content fills ¾ of the volume of the collection reservoir, then the control unit begins providing a warning indicating that the reservoir is substantially full.

The control unit 230 includes an internal storage unit 244 (e.g., embodied in a hardware device), or alternatively may be connected to a local, external storage unit 246 (disposed within the housing), to track and save patient information, patient health and dental records, and data concerning the use of the oral care system by the patient(s). As described above, the control unit tracks data regarding flow of fluids through the oral care system 200, which may be saved in the storage unit. The control unit monitors and records the date and time in which a patient(s) undergoes a cleaning cycle/session. Further, information regarding whether a cleaning session was completed, interrupted, or failed to complete is recorded. During instances of failure or interruption in the cleaning session, the control unit also records the particular problem and source of failure. The control unit may be configured to provide patients and users reminders, either an audible reminder or a visual reminder on a display unit 290 (FIGS. 6-11), about scheduled cleaning sessions and/or missed cleaning sessions.

In some embodiments, the control unit 230 keeps track of the operational status of the oral care system. If there are issues that affect or potentially affect the proper functioning of the oral care system, the control unit provides warning indicators (e.g., audible or visual). For example, the control unit issues warnings when: (1) the oral hygiene system (i.e., mouthpiece) is connected improperly to the gooseneck arm, or alternatively to inlet and outlet tubes; (2) one or more irrigant bottles are improperly connected to the socket fittings; (3) fluid levels of the irrigation solutions within the bottles are low; (4) when a collection reservoir (for collecting saliva and used irrigation solution evacuated from the mouthpiece) is nearly full; and/or (5) when the pumps (for directing flow of irrigation solutions from the bottles to the mouthpiece and/or for evacuating saliva and used irrigation solutions from the mouthpiece) are malfunctioning. The control unit maintains a record of system maintenance and notifies the user when the fluid lines in the oral care system require cleaning (e.g., flush fluid lines with cleaning solution) and when the mouthpiece requires cleaning (e.g., cleaning in a separate cleaning device such as an autoclave).

In some embodiments, the oral care system 200 includes a local power source 240, such as a rechargeable battery or energy cell, to power the various components of the oral care system (e.g., irrigation pumps 210, control valve 212, check valves 214, evacuation pump 225, transmitter 236, and oral hygiene system 100). The power source is positioned within the housing (FIGS. 6-8) may be connected to the control unit 230 via a power line 234. The control unit 230 may include a voltage regulator to provide voltage regulation to stabilize voltages used by the processor and other components of the oral care system 200. In other embodiments, the power source 240 is connected directly to one or more of the components of the oral care system 100 without first being routed to the control unit 230.

In addition to the power source 240, the oral care system 200 includes an electrical plug 242 (FIGS. 6-11) which is connectable to an electrical socket to receive power from an external source. The electricity provided through the plug 242 may be used to power the oral care system 200 as well as recharge the power source 240.

The communication line 232 between the control unit 230 and the oral hygiene system 100 may be adapted to provide electricity for powering the actuators 20 and electrodes 30, for example when the power source 21 of the oral hygiene system 100 has a low charge. In some embodiments, the electricity provided through the communication line 232 may be used to recharge the power source 21, or alternatively, replace the need for the power source 21.

The control unit 230 is configured to monitor the power levels of all power sources present in the oral care system 200, including the power source 240 disposed in the housing and the power source 21 of the oral hygiene system 100. When either power source reaches a low-battery state and requires charging, the control unit 230 provides an audible and/or visual warning indicator.

In some embodiments, the control unit 230 is configured to communicate through a network 250 (e.g., Internet) with at least one remote server 252, transmitting the data that has been tracked and saved by the control unit (e.g., patient information, patient health and dental records, and data concerning the use of the oral care system by the patient) to the server 252. The server, therefore, records information regarding the daily administration of the oral care system for each of one or more patients and the dental health of each of the one or more patients. The server can be any type of patient health record server, such as an electronic Medication Administration Record (eMAR) server. The oral care system 200 includes a wireless transmitter 236 (e.g., Wi-Fi, Bluetooth) so that it can communicate wirelessly with the remote server 252. Alternatively, the oral care system 200 can connect to the remote server through a wired connection (e.g., Ethernet, fiber-optic cable). The server 252 may be accessible by a patient's doctor, dentist, care-taker, and/or health care provider in order to review the patient's dental health and progress. Through the server, the patient's doctor or dentist can transmit a text, audio and/or video message to the oral care system 200, providing the patient or user with recommendations on adjusting future cleaning sessions. In some embodiments, the server 252 provides for the patient's doctor or dentist to remotely configure the oral care system 200 to perform a prescribed cleaning session, thereby eliminating the need for the patient to manually input the adjustments. In other embodiments, the connection between the oral care system and the remote server enables real-time communication between the patient and the patient's doctor, dentist, care-taker, and/or health care provider.

Figure 6:
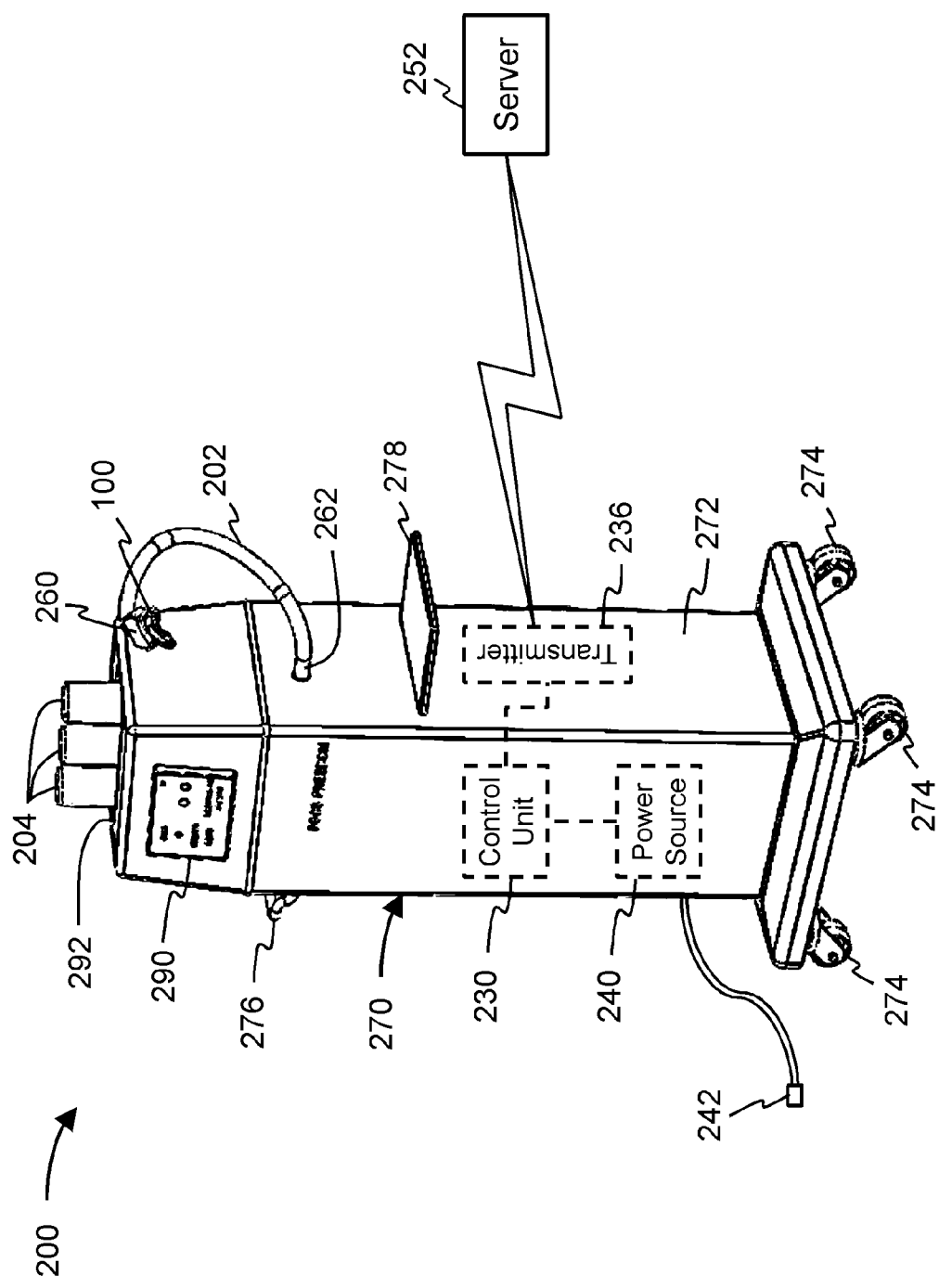
FIG. 6 is a perspective view of the oral care system of FIG. 5 in a mobile dental cart.
Figure 7:
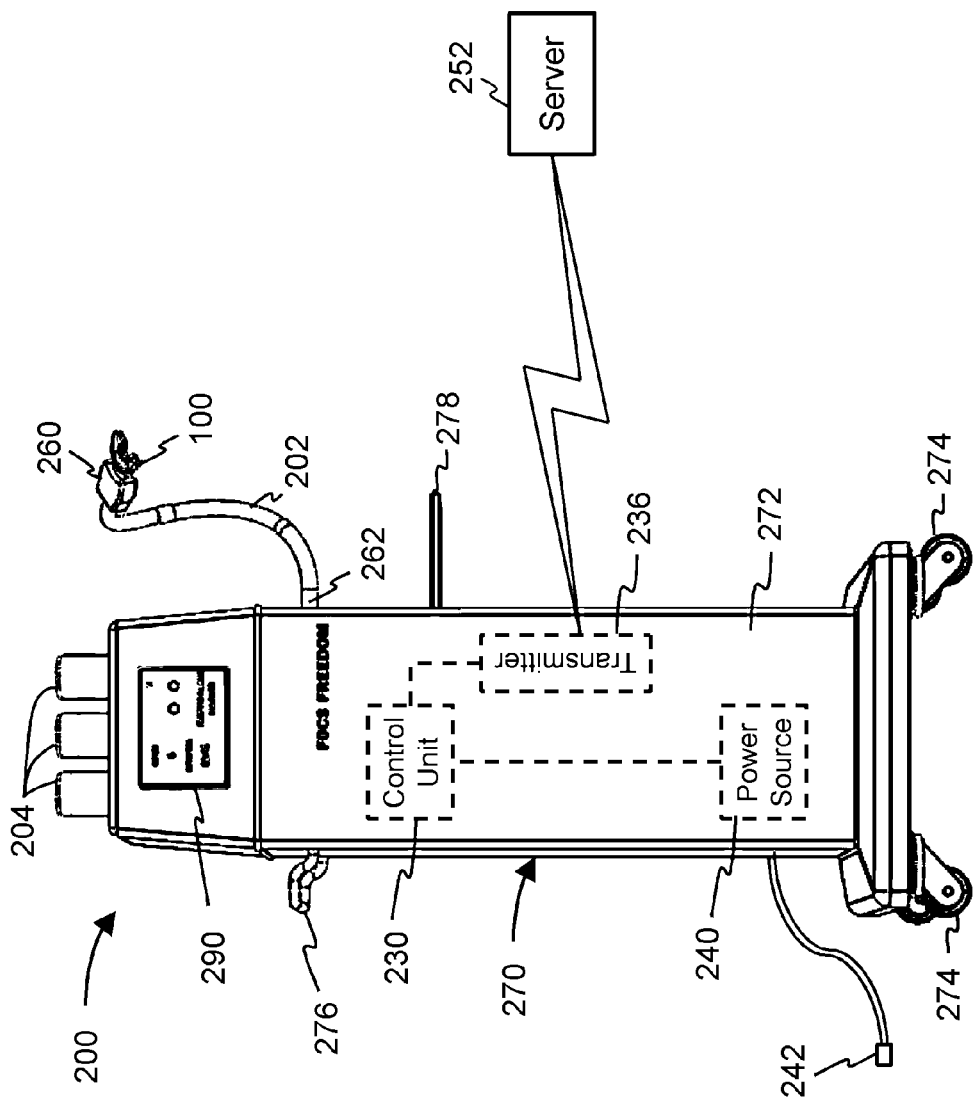
FIG. 7 is a front view of the oral care system of FIG. 5 in a mobile dental cart.
Figure 8:
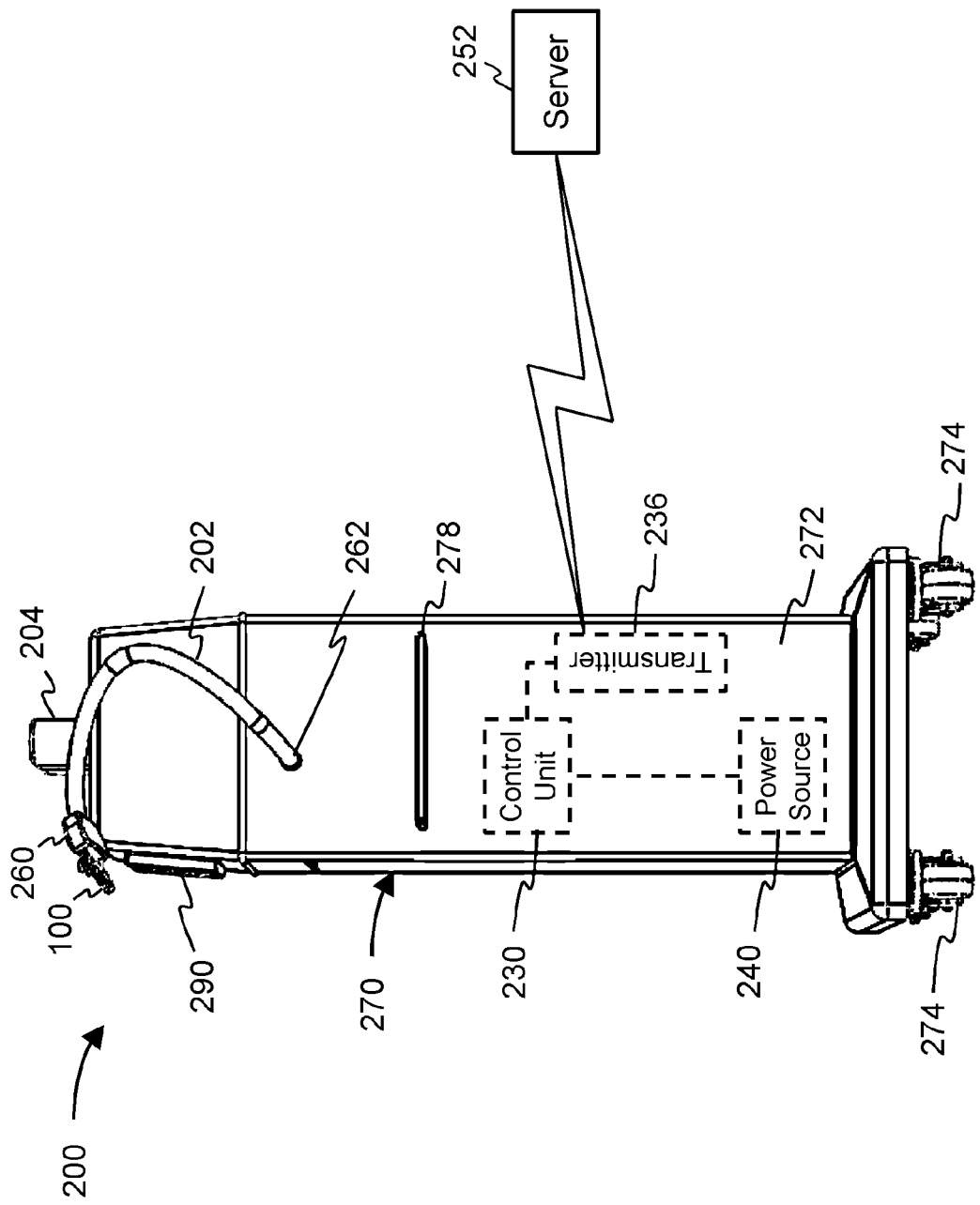
FIG. 8 is a side view of the oral care system of FIG. 5 in a mobile dental cart.

Referring to FIGS. 6-8, the oral care system 200 is configured such that the housing is a mobile dental cart 270. The mobile dental cart 270 comprises a tower with exterior surface 272 and a plurality of wheels 274 mounted to the base of the tower. The socket fittings 208 are positioned at the top of the tower of the dental cart 270, such that the irrigant bottles 204 may be easily installed into their respective socket fittings in an inverted position. The exterior mounting of the irrigant bottles is beneficial because it allows for visual checking of the fluid levels of the irrigation solutions. In some embodiments, the top of the dental cart 270 is designed with a recessed section 292, within which the sockets fittings are located. The recessed section 292 with substantially vertical walls define a container which is adapted collect irrigation solution that may spill or leak out during installation and removal of an irrigant bottle to/from the socket fitting.

The wheels 274 of the mobile dental cart 270 can be manually locked in order to prevent movement of the oral care system 200. In some embodiments, the control unit 230 automatically locks the wheels when a cleaning session is initiated, thereby ensuring that the dental cart 270 does not shift as the patient's teeth are being cleaned. Once the cleaning session ends, the control unit 230 unlocks the wheels so that the dental cart 270 can be moved. A shelf 278 is also mounted to the exterior surface 272, thereby providing a horizontal surface on which objects may be placed. The dental cart also includes a push-pull handle 276, which allows for the oral care system 200 to be easily and quickly moved from one patient to another within a work site environment, including a dentist office, nursing home or hospital.

On the exterior surface 272 of the housing, a display monitor 290, such as a touch-screen, is provided. The display monitor provides the status of the oral care system 200, showing how much time is left in a cleaning session, whether a cleaning session has been initiated or terminated, and whether the cleaning session successfully completed or failed due to a malfunction. The display monitor may also show fluid levels of each of the irrigant bottles and the fluid level of the collection reservoir. Further, the warning indicators discussed above may be displayed on the monitor 290. In some embodiments, a patient or user can manually adjust operation of the oral care system 200 through the display monitor, selecting different options to program the length of cleaning session and which modalities are to be performed.

Figure 9:
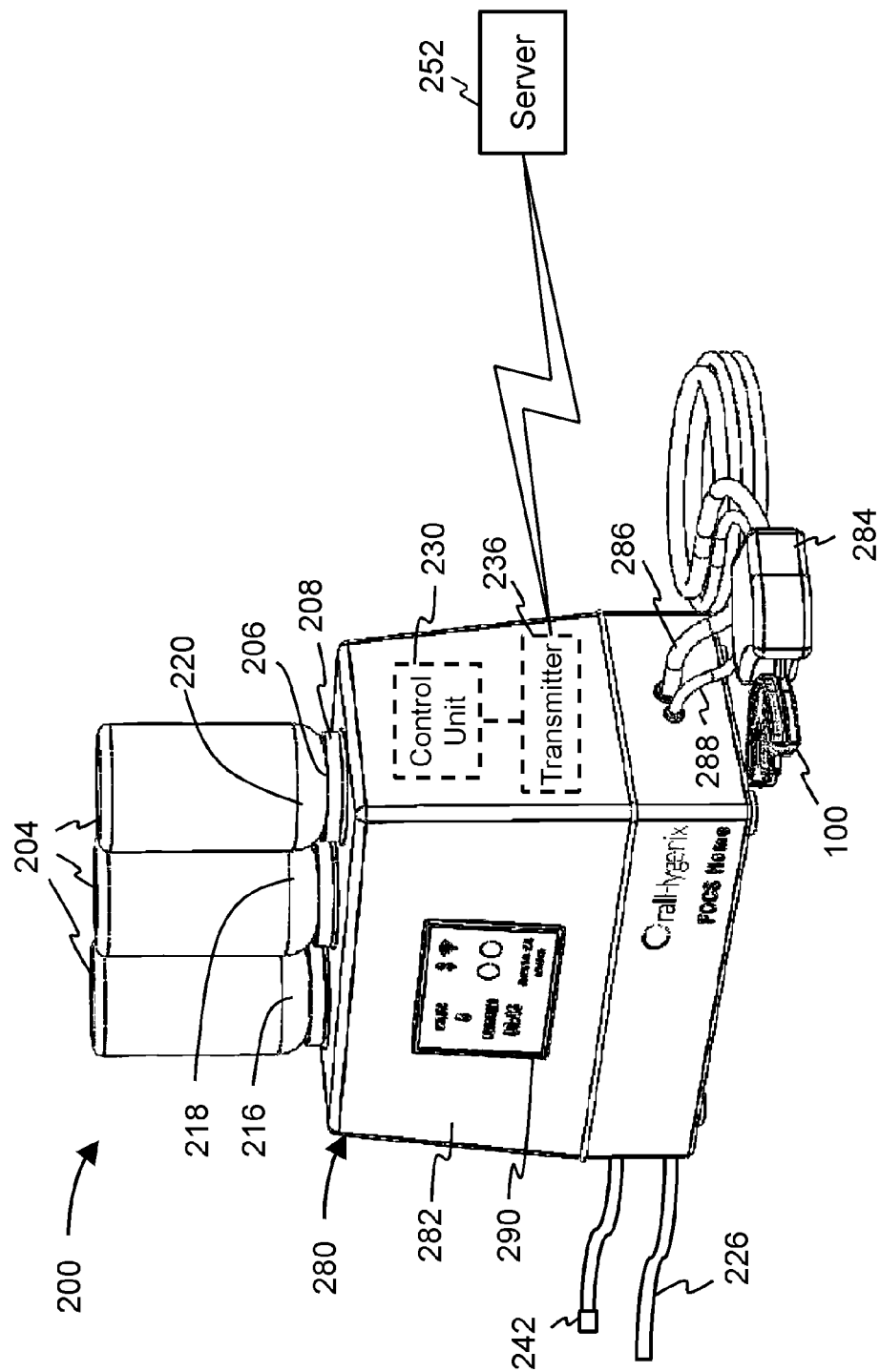
FIG. 9 is a perspective view of the oral care system of FIG. 5 as a countertop unit.
Figure 10:
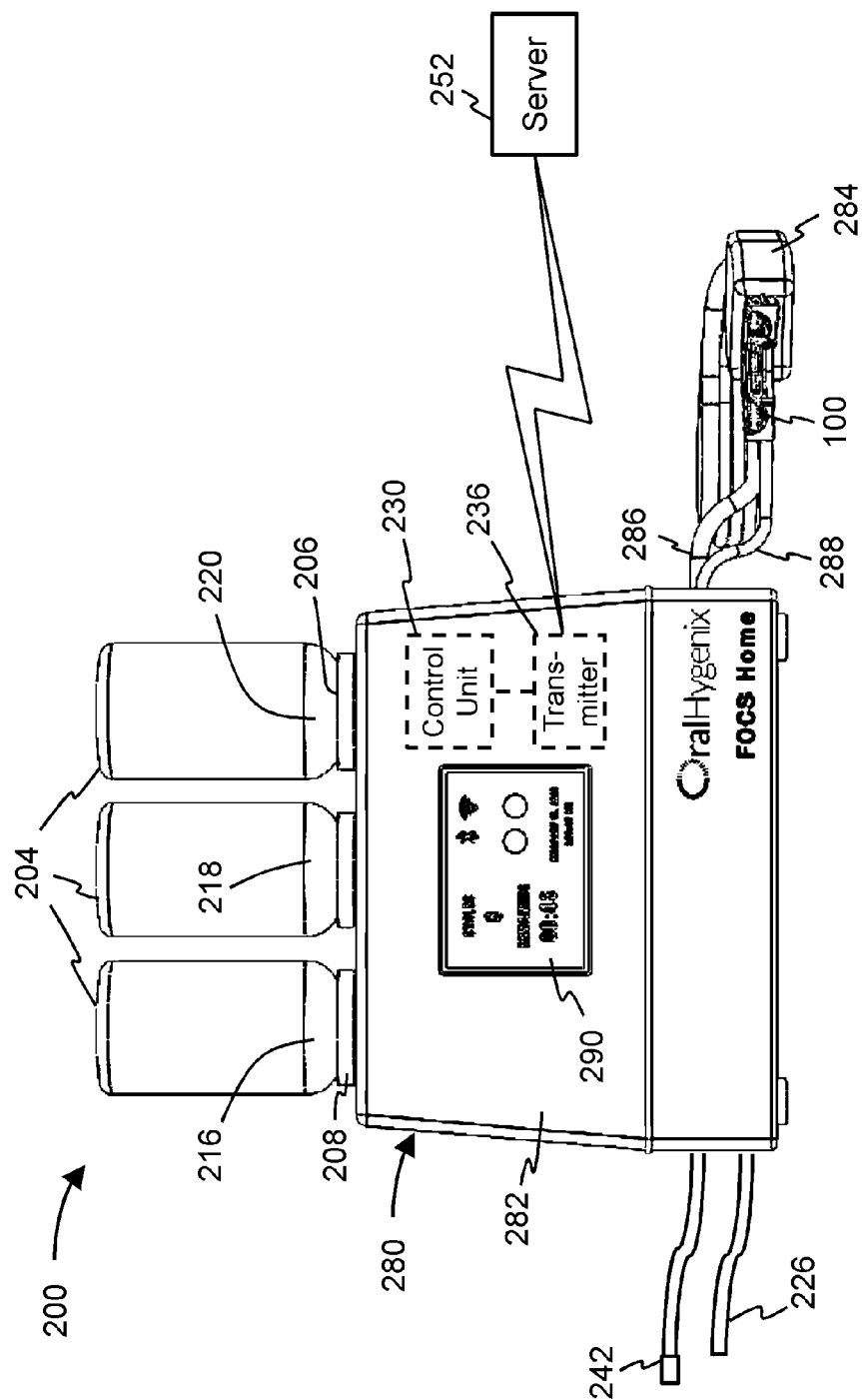
FIG. 10 is a front view of the oral care system of FIG. 5 as a countertop unit.
Figure 11:
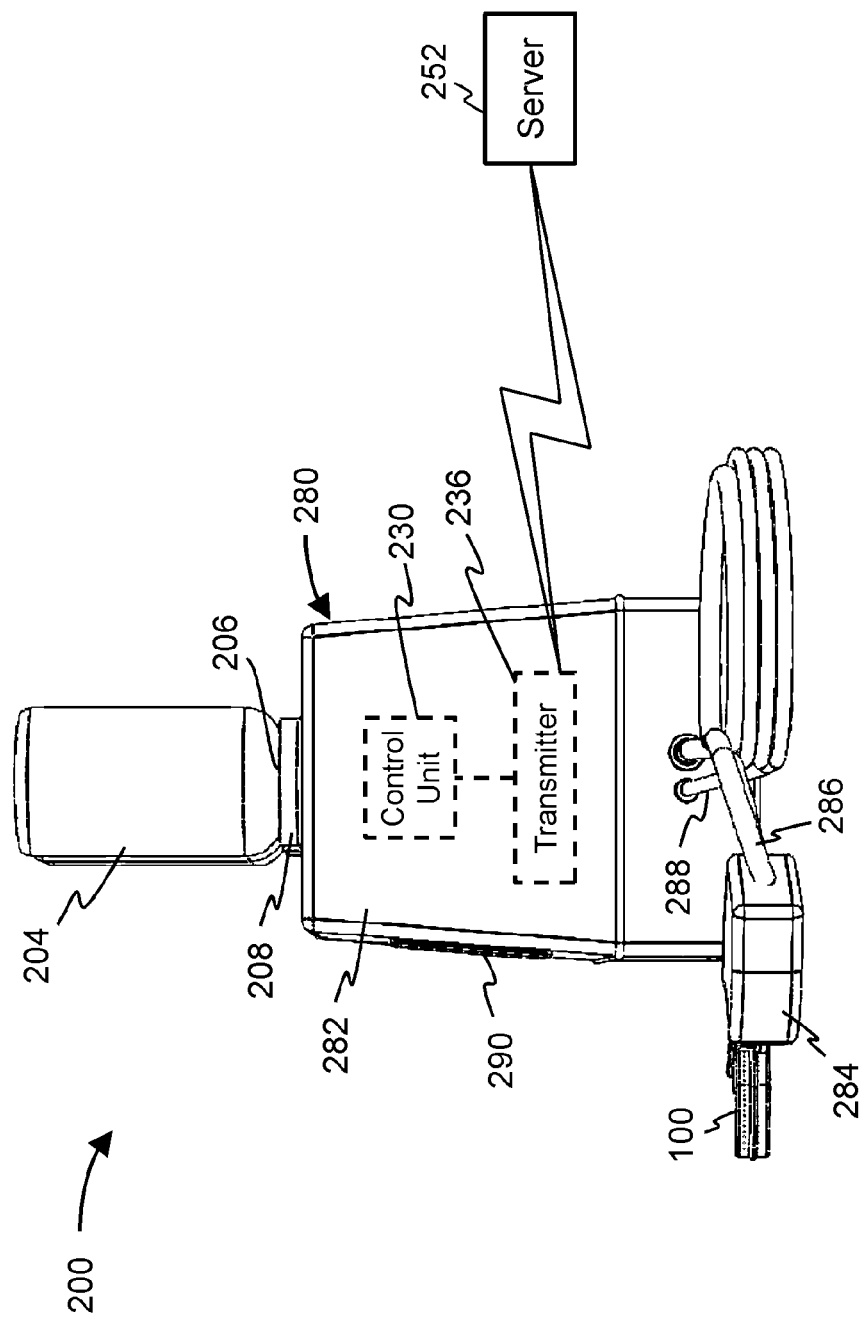
FIG. 11 is a side view of the oral care system of FIG. 5 as a countertop unit.

Referring to FIGS. 9-11, the oral care system 200 is configured such that the housing is a portable countertop housing 280. The countertop housing 280 has similar features as the mobile dental cart 270, except the countertop housing has a substantially smaller form factor and does not include wheels. The countertop housing 280 replaces the gooseneck arm 202 with flexible inlet and outlet hoses 286, 288. At the distal ends of the hoses 286, 288, a mouthpiece coupler 284 releasably couples to the oral hygiene system 100. The countertop housing 280 does not include an internal power source (e.g., rechargeable battery 240). It only has the electrical plug 242 to receive power from an electrical socket. By excluding an internal power source, the countertop housing weighs substantially less than the dental cart version of the oral care system. Moreover, the countertop housing does not include a collection reservoir. Instead, the drain hose 226 extends outside the exterior surface 282 of the countertop housing 280 so that the distal end of the drain hose may be positioned directly into a drain or sink.

Although the invention has been described with reference to particular arrangement of parts, features, and the like, these are not intended exhaust all possible arrangements or features, and indeed many modifications and variations will be ascertainable to those of skill in the art.

What is claimed is:

1. An oral care system for cleaning teeth and gums, the system comprising:
    a housing,
    an oral hygiene unit, said oral hygiene unit comprising:
        a mouthpiece having at least one arcuate channel adapted to receive and substantially surround a dental arch including an entire row of maxillary or mandibular teeth and gums, said mouthpiece is configured to maintain position around the dental arch without intervention during operation of the oral hygiene unit; and
        an insert releasably coupled to said arcuate channel of said mouthpiece, said insert having a U-shaped cross section formed by two vertical walls and a base wall;
        said mouthpiece includes a mechanical modality, an iontophoretic modality and a disinfection modality, wherein the mechanical modality brushes the teeth and gums through direct contact and dislodges food debris, the iontophoretic modality breaks up plaque buildup, and the disinfection modality irrigates said teeth and gums; and
    a gooseneck arm attached to the housing and releasably coupling the oral hygiene unit to the housing, said gooseneck arm being adjustable to hold the oral hygiene unit at a defined position and orientation relative to the housing;
    a control unit disposed in said housing programmed to actuate and control a sequence and duration of the actuation of the modalities to perform a cleaning session, wherein the control unit, according to the programmed sequence and duration, transmits control signals to at least one of said mechanical, iontophoretic, or disinfection modalities;
    said control unit monitoring and tracking data, including an operational status of the oral care system and information concerning the cleaning session, and storing the data tracked by said control unit;
    a transmitter in said housing communicating said data tracked by said control unit to a remote server, said remote server recording at least a portion of the information concerning the cleaning session in a record associated with a particular patient.

2. The oral care system of claim 1, further comprising:
    at least one socket fitting which is disposed on an exterior surface of the housing;
    at least one irrigant bottle containing at least one irrigation solution, the at least one irrigant bottle configured to be releasably connected in the at least one socket fitting, wherein the connection of the irrigant bottle and the socket fitting provides flow of the irrigation solution to the oral hygiene unit for use in one or more of said mechanical, iontophoretic, or disinfection modalities.

3. The oral care system of claim 2, wherein the at least one socket fitting has a lock and key construction which locks and retains the at least one irrigant bottle in an inverted position, the lock and key construction providing shape metrics for the at least one socket fitting to mate only with the at least one irrigant bottle having a closure cap with a shape that complements the shape metrics.

4. The oral care system of claim 2, wherein, in response to connection of the at least one socket fitting with the at least one irrigant bottle, the at least one socket fitting and a closure cap of the at least one irrigant bottle provide for controlled release of the at least one irrigation solution from the at least one irrigant bottle in an inverted position, the closure cap and the socket fitting forming a fluid-tight seal.

5. The oral care system of claim 2, further comprising one or more inlet flow lines communicating the at least one irrigation solution to at least one inlet port disposed in at least one of said vertical walls of said insert,
    the inlet flow line extending from the at least one socket fitting and through the gooseneck arm and being releasably coupled to at least one supply channel which is disposed in the oral hygiene unit and is fluidly connected to the at least one inlet port.

6. The oral care system of claim 5, further comprising at least one irrigation pump disposed within the housing and in fluid communication with the one or more inlet flow lines, the irrigation pump producing fluid flow from the at least one irrigant bottle to the oral hygiene unit.

7. The oral care system of claim 6, further comprising at least one control valve disposed within the one or more inlet flow lines downstream from the at least one irrigation pump, the control valve regulating fluid flow and pressure of the at least one irrigation solution.

8. The oral care system of claim 2, wherein the housing has three socket fittings and the at least one irrigant bottle comprises three irrigant bottles, each socket fitting being configured to receive one of the three irrigant bottles;

wherein the socket fittings have a lock and key construction which locks and retains one of the three irrigant bottles in an inverted position, the lock and key construction providing shape metrics for the socket fittings to mate with one of the three irrigant bottles, the three irrigant bottles having closure caps with shapes complementing the shape metrics of the socket fittings.

9. The oral care system of claim 8, wherein each socket fitting has its own unique lock and key construction providing shape metrics for the respective socket fitting to mate with only one of the three irrigant bottles having a closure cap with a shape complementing the shape metrics of the respective socket fitting.

10. The oral care system of claim 1, further comprising:
one or more outlet flow lines configured to evacuate at least one irrigation solution released in the oral hygiene unit through at least one outlet port disposed in the base wall of said insert; and
at least one evacuation pump configured to generate a suction force to direct the at least one irrigation solution released in the oral hygiene through the one or more outlet flow lines for disposal.

11. The oral care system of claim 10, further comprising a collection reservoir disposed in the housing, said collection reservoir being configured to collect the at least one irrigation solution transmitted through the one or more outlet flow lines, wherein said collection reservoir is removable from within the housing to dispose the at least one irrigation solution contained in the collection reservoir.

12. The oral care system of claim 1, wherein the control unit transmits control signals to at least one actuator disposed in said mouthpiece to vibrate a plurality of brush heads attached the vertical walls and base wall of the insert at a predetermined frequency.

13. The oral care system of claim 1, wherein the control unit transmits control signals to at least one electrode disposed in said mouthpiece to apply the iontophoretic modality, said control signals initiating and terminating an electrical charge at a predetermined voltage and current for depolarizing adherence bonding of plaque buildup.

14. The oral care system of claim 1, wherein the control unit transmits control signals to at least one irrigation pump and at least one control valve to generate and regulate flow of at least one irrigation solution in one or more inlet flow lines and to eject the at least one irrigation solution by at least one inlet port, which is disposed in the oral hygiene system and is communicatively connected to the one or more inlet flow lines; and wherein the control unit is configured to transmit control signals to at least one evacuation pump to extract the at least one irrigation solution through at least one outlet port disposed in the oral hygiene system after being ejected, the control unit controlling the suction force applied to an outlet flow line by the evacuation pump.

15. The oral care system of claim 1, further comprising at least one pressure sensor in one of the insert or the mouthpiece of the oral hygiene unit, wherein the control unit performs at least one of the modalities upon detecting pressure exerted on the pressure sensor of the oral hygiene unit by teeth.

16. The oral care system of claim 1, wherein the information concerning the cleaning session includes the duration of the cleaning session, time remaining in the cleaning session, whether the cleaning session completed or failed to complete.

17. The oral care system of claim 1, further comprising a display monitor mounted to an exterior surface of the housing, the display monitor showing said data tracked by the control unit and providing indicators about malfunctions and maintenance needed for continued operation of the oral care system.

18. An oral care system for cleaning teeth and gums, the system comprising:
a dental cart, said dental cart comprising a tower mounted on a plurality of wheels;
an oral hygiene unit, said oral hygiene unit comprising:
a mouthpiece having at least one arcuate channel adapted to receive and substantially surround a dental arch including an entire row of maxillary or mandibular teeth and gums, said mouthpiece is configured to maintain position around the dental arch without intervention during operation of the oral hygiene unit; and
an insert releasably coupled to said arcuate channel of said mouthpiece, said insert having a U-shaped cross section formed by two vertical walls and a base wall;
said mouthpiece includes a mechanical modality, an iontophoretic modality and a disinfection modality, wherein the mechanical modality brushes the teeth and gums through direct contact and dislodges food debris, the iontophoretic modality breaks up plaque buildup, and the disinfection modality irrigates said teeth and gums;
a gooseneck arm attached to the dental cart and releasably coupling the oral hygiene unit to the dental cart, said gooseneck arm being adjustable to hold the oral hygiene unit at a defined position and orientation relative to the dental cart; and
at least one irrigant bottle releasably mounted in an inverted position on a top surface of the tower, said irrigant bottle containing at least one irrigation solution for use in one or more of said mechanical, iontophoretic, or disinfection modalities;
a control unit disposed in said housing programmed to actuate and control a sequence and duration of the actuation of the modalities to perform a cleaning session, wherein the control unit, according to the programmed sequence and duration, transmits control signals to at least one of said mechanical, iontophoretic, or disinfection modalities;
said control unit monitoring and tracking data, including an operational status of the oral care system and information concerning the cleaning session, and storing the data tracked by said control unit;
a transmitter in said housing communicating said data tracked by said control unit to a remote server, said remote server recording at least a portion of the information concerning the cleaning session in a record associated with a particular patient.

19. The oral care system of claim 18, further comprising a collection reservoir removably disposed within the dental cart, the collection reservoir collecting the at least one irrigation solution after the at least one irrigation solution is used in the one or more mechanical, iontophoretic, or disinfection modalities and is evacuated from the oral hygiene unit.

20. The oral care system of claim 18, further comprising:
a display monitor mounted on an exterior surface of the dental cart, the display monitor showing data tracked by the control unit; and
a power source mounted within the dental cart, the power source providing power to the control unit, the display monitor and the oral hygiene unit.

21. An oral care system for cleaning teeth and gums, the system comprising:
- a countertop housing providing a base of the oral care system;
- an oral hygiene unit, said oral hygiene unit comprising:
  - a mouthpiece having at least one arcuate channel adapted to receive and substantially surround a dental arch including an entire row of maxillary or mandibular teeth and gums, said mouthpiece is configured to maintain position around the dental arch without intervention during operation of the oral hygiene unit; and
  - an insert releasably coupled to said arcuate channel of said mouthpiece, said insert having a U-shaped cross section formed by two vertical walls and a base wall;
  - said mouthpiece includes a mechanical modality, an iontophoretic modality, and a disinfection modality, wherein the mechanical modality brushes the teeth and gums through direct contact and dislodges food debris, the iontophoretic modality breaks up plaque buildup, and the disinfection modality irrigates said teeth and gums;
- an inlet-outlet hose attached to the countertop housing and releasably coupling the oral hygiene unit to the countertop housing, said inlet-outlet hose being flexible;
- at least one irrigant bottle releasably mounted in an inverted position on a top surface of the countertop housing, said irrigant bottle containing at least one irrigation solution for use in one or more of said mechanical, iontophoretic, or disinfection modalities;
- at least one irrigation pump disposed in the countertop housing, said at least one irrigation pump producing fluid flow from the at least one irrigant bottle to the oral hygiene unit through one or more inlet flow lines; and
- at least one drain hose extending out of the countertop housing, said drain hose providing drainage of the at least one irrigation solution after the at least one irrigation solution is used in the one or more mechanical, iontophoretic, or disinfection modalities and is evacuated from the oral hygiene unit;
- a control unit disposed in said housing programmed to actuate and control a sequence and duration of the actuation of the modalities to perform a cleaning session, wherein the control unit, according to the programmed sequence and duration, transmits control signals to at least one of said mechanical, iontophoretic, or disinfection modalities;
- said control unit monitoring and tracking data, including an operational status of the oral care system and information concerning the cleaning session, and storing the data tracked by said control unit;
- a transmitter in said housing communicating said data tracked by said control unit to a remote server, said remote server recording at least a portion of the information concerning the cleaning session in a record associated with a particular patient.

22. The oral care system of claim 21, further comprising:
- a display monitor mounted on an exterior surface of the countertop housing, the display monitor showing data tracked by the control unit; and
- an electrical plug connected to the countertop housing, the electrical plug receiving power from an external source to provide power to the control unit, the display monitor and the oral hygiene unit.

23. The oral care system of claim 1, said control unit receiving data indicative of the programmed sequence and duration from the remote server.

* * * * *